(12) United States Patent
Jaroch

(10) Patent No.: US 10,806,893 B2
(45) Date of Patent: Oct. 20, 2020

(54) GUIDING CATHETER HAVING SHAPE-RETENTIVE DISTAL END

(71) Applicant: Surefire Medical, Inc., Westminster, CO (US)

(72) Inventor: David Benjamin Jaroch, Arvada, CO (US)

(73) Assignee: Surefire Medical, Inc., Westminster, CO (US)

( * ) Notice: Subject to any disclaimer, the term of this patent is extended or adjusted under 35 U.S.C. 154(b) by 243 days.

(21) Appl. No.: 15/864,978

(22) Filed: Jan. 8, 2018

(65) Prior Publication Data

US 2018/0193591 A1 Jul. 12, 2018

Related U.S. Application Data

(60) Provisional application No. 62/444,554, filed on Jan. 10, 2017.

(51) Int. Cl.
*A61M 25/00* (2006.01)
*A61M 25/06* (2006.01)

(52) U.S. Cl.
CPC ...... *A61M 25/008* (2013.01); *A61M 25/0013* (2013.01); *A61M 25/0041* (2013.01); *A61M 25/0051* (2013.01); *A61M 25/0068* (2013.01); *A61M 25/0662* (2013.01); *A61M 2205/0266* (2013.01)

(58) Field of Classification Search
CPC .......... A61M 25/0054; A61M 25/0013; A61M 25/0053; A61M 25/008
See application file for complete search history.

(56) References Cited

U.S. PATENT DOCUMENTS

| | | | |
|---|---|---|---|
| 4,655,771 A | 4/1987 | Wallsten | |
| 5,071,407 A | 12/1991 | Termin et al. | |
| 5,496,277 A | 3/1996 | Termin et al. | |
| 5,607,466 A | 3/1997 | Imbert et al. | |
| 5,725,571 A | 3/1998 | Imbert et al. | |
| 5,755,769 A | 5/1998 | Richard et al. | |
| 5,957,974 A | 9/1999 | Thompson et al. | |
| 6,500,203 B1 | 12/2002 | Thompson et al. | |

(Continued)

FOREIGN PATENT DOCUMENTS

DE 8910603 U1 12/1989
EP 0533511 A1 3/1993

(Continued)

*Primary Examiner* — Nathan R Price
*Assistant Examiner* — Melissa A Snyder
(74) *Attorney, Agent, or Firm* — Gordon & Jacobson, P.C.

(57) ABSTRACT

A guiding catheter has a proximal portion constructed of a tubular braid and a shape-retentive distal portion including a superelastic hypotube cut to define particular mating, support, shape-retentive and flexibility characteristics. A tubular liner extends through both of the tubular braid and the hypotube. The hypotube is joined to the braid using a mechanical interlock that has high torque transfer from the braid to the hypotube. A short portion of high stiffness polymer tube is provided at a joint between the braid and the hypotube. A polymeric outer jacket is provided over the proximal and distal portions, including the polymer tube. The jacket is heat set over the hypotube to remove residual stress.

13 Claims, 22 Drawing Sheets

(56) References Cited

U.S. PATENT DOCUMENTS

| | | | |
|---|---|---|---|
| 6,596,122 B1 * | 7/2003 | Savitski | B29C 65/148 |
| | | | 156/304.2 |
| 6,652,491 B1 * | 11/2003 | Walker | A61M 25/0102 |
| | | | 604/164.01 |
| 6,673,090 B2 | 1/2004 | Root et al. | |
| 6,746,489 B2 | 6/2004 | Dua et al. | |
| 6,858,024 B1 * | 2/2005 | Berg | A61M 25/0013 |
| | | | 604/525 |
| 7,118,600 B2 | 10/2006 | Dua et al. | |
| 7,326,226 B2 | 2/2008 | Root et al. | |
| 7,425,215 B2 | 9/2008 | Boyle et al. | |
| 7,678,223 B2 * | 3/2010 | Strong | B32B 38/10 |
| | | | 156/272.8 |
| 10,124,087 B2 * | 11/2018 | De Silva | C08L 23/06 |
| 2003/0233115 A1 | 12/2003 | Eversull et al. | |
| 2005/0004517 A1 | 1/2005 | Courtney et al. | |

FOREIGN PATENT DOCUMENTS

| | | |
|---|---|---|
| EP | 0554579 A1 | 8/1993 |
| EP | 0416662 B1 | 3/1996 |
| FR | 2652267 A1 | 3/1991 |
| GB | 2020557 B | 1/1983 |

\* cited by examiner

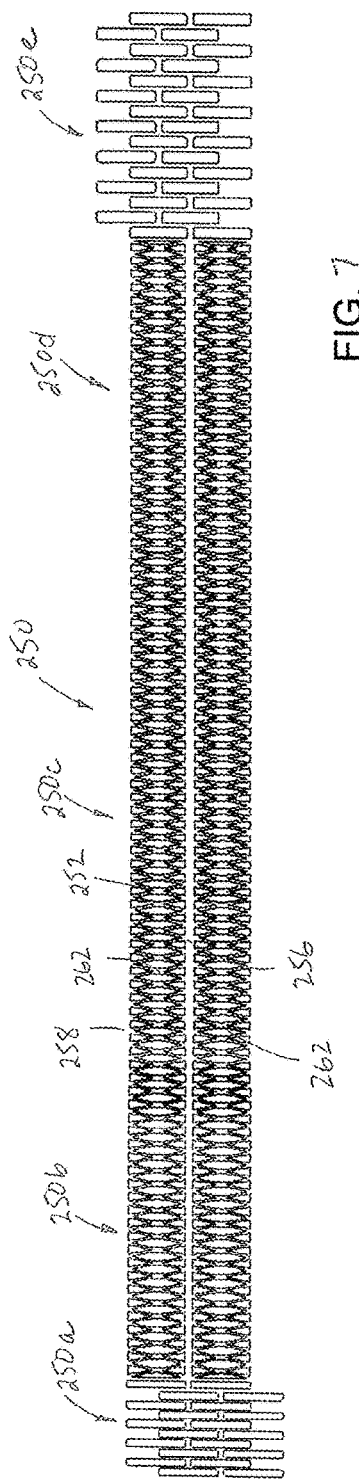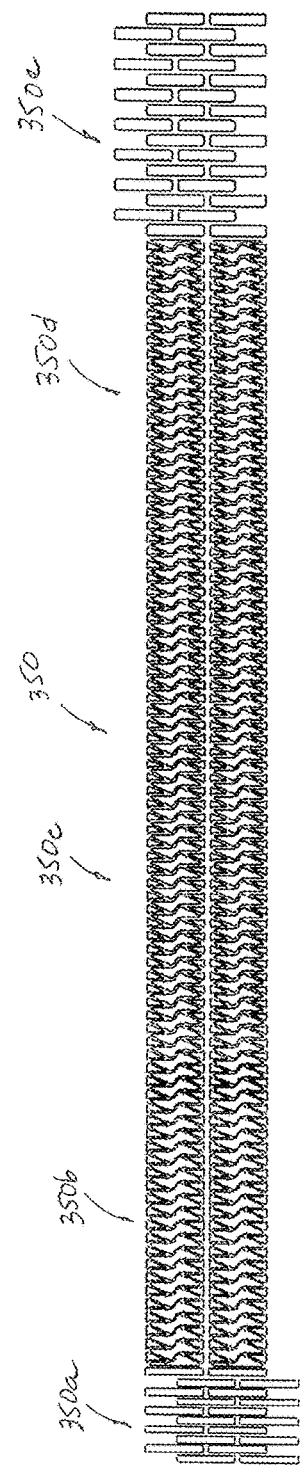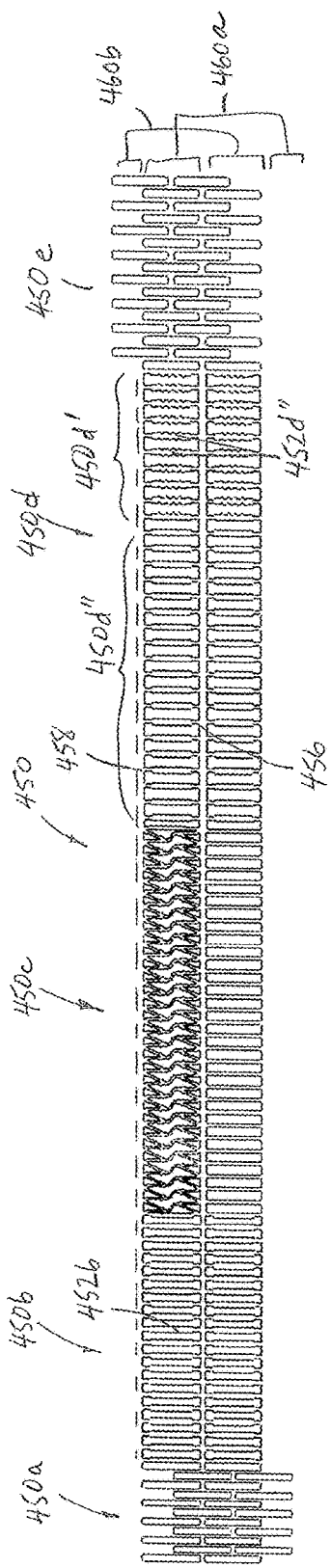

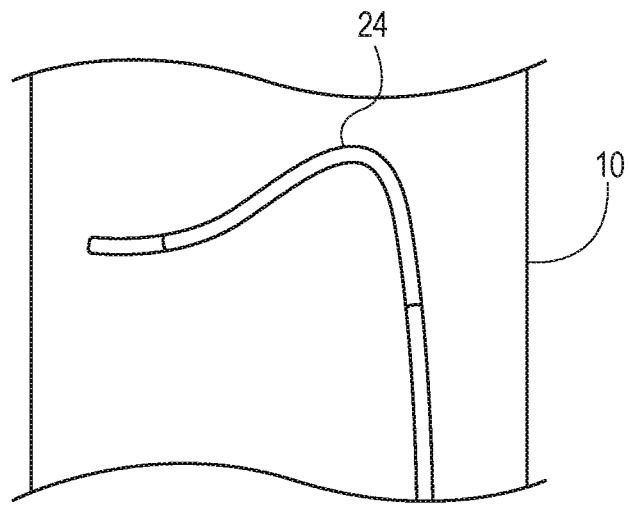
FIG. 29
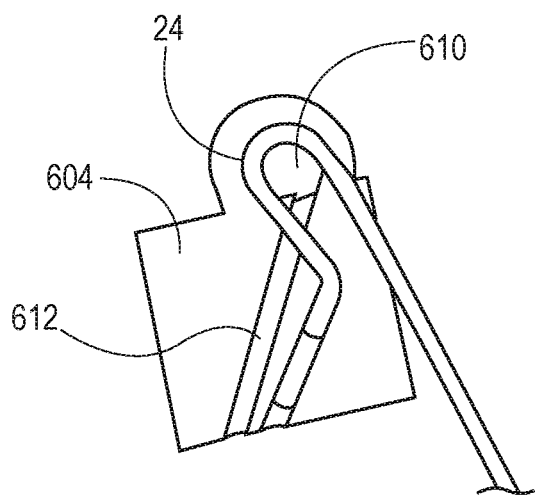 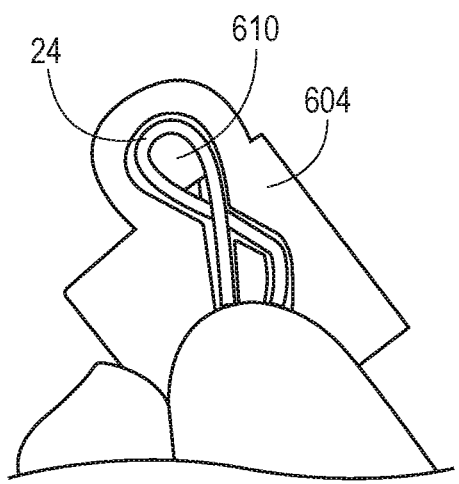
FIG. 30　　　　　FIG. 31

GUIDING CATHETER HAVING SHAPE-RETENTIVE DISTAL END

CROSS-REFERENCE TO RELATED APPLICATION

This application claims benefit to U.S. Provisional Ser. No. 62/444,554, filed Jan. 10, 2017, which is hereby incorporated by reference herein in its entirety.

BACKGROUND OF THE INVENTION

1. Field of the Invention

The present invention relates to catheters. More particularly, the present invention relates to guiding catheters that facilitate the introduction and support of secondary devices passed through their inner lumen.

2. State of the Art

Typical interventional radiology procedures involve the introduction of catheters into the circulatory system, typically using femoral or radial access points. One of the primary tools used in such procedures are angiographic catheters that are intended to act as a fluid conduit for contrast mapping of the patient's anatomy prior to treatment. Such catheters are often designed with uniquely shaped distal segments intended to facilitate tracking and placement of the device within specific points of the patient's anatomy.

Angiographic catheters are typically designed to accommodate a guidewire of 0.035 inch or 0.038 inch diameter, which are used to advance the catheter though the anatomy prior to final placement. This small inner lumen size requirement allows angiographic catheters to be designed with thick walls that serve to provide mechanical support to the device and allow for the shaped distal segments to have a high degree of original shape retention upon straightening and initial introduction to the anatomy.

Angiographic catheters, being intended as a fluid conduit for a contrast agent, are typically not lined with materials that reduce friction when interfaced with a solid material, as is the case during introduction of a guidewire or microcatheter through an angiographic catheter. In these instances friction is reduced but not eliminated by a hydrophilic coating applied to the outer surface of the guidewire or microcatheter.

In contrast, guiding catheters are specifically designed to facilitate the introduction and support of secondary devices passed through their inner lumen. Such secondary devices may include, by way of example, guidewires, microcatheters, lasers, and stents. Like angiographic catheters, guiding catheters often have a shaped distal segment intended to ease placement within desired anatomy and provide additional support to secondary device introduction.

In order to further facilitate introduction of secondary devices with a range of sizes and surface geometries into the lumen of a guide catheter, guiding catheters are designed to maximize inner lumen space and minimize friction using a variety of low surface energy lining material such as polytetrafluoroethylene (PTFE). The relatively large inner lumen size corresponds to a subsequent reduction in wall thickness. The catheter walls are then typically reinforced with wire coils or braid to retain acceptable mechanical properties during use. However, the reduced overall wall thickness and the lack of volume of high shape retentive material limits distal shape geometry and support.

Shape retention refers to how well a device maintains its original shape during clinical usage. As the shape is intended to conform with specific anatomies, maintenance of the shape though the procedure is critical for initial ease of placement and usage of the device. However, tests have shown that on-market guiding catheters have a significant loss in shape retention. By way of example, testing has shown that an on-market angiographic catheter 2 having a distal tip 4 pre-shaped into a 180° reverse turn (Prior Art FIG. 1A), after being straightened in a manner that simulates introduction into the patient, will only return to a 145° reverse turn (Prior Art FIG. 1B). Moreover, on-market guiding catheters exhibit even worse performance. By way of example, catheter 6 having a distal tip 8 similarly pre-shaped into a 180° reverse turn (as distal tip 4), will only return to a 110° reverse turn after straightening (Prior Art FIG. 1C). This could lead to difficulties in guiding the secondary devices to the vessels of interest.

Support, namely backup support, refers to the amount of support or resistance to deflection from a set shape the guiding catheter provides when an accessory device is passed through the lumen of the guiding catheter. In severe catheter shapes, such as the 180° bend referenced above, the guiding catheter redirects an upward pushing force downward into the vasculature. Backup support is a measure of how much force can be redirected and how well the direction of force is maintained.

SUMMARY

A guiding catheter is provided having a length with a proximal portion and a distal portion. The proximal portion is constructed with a tubular braid. The distal portion comprises a hypotube cut to define particular mating, support, shape-retentive and flexibility characteristics. A polymer tubular liner extends through both of the tubular braid and the hypotube. A polymer outer jacket extends over both of the proximal and distal portions.

The shape-retentive hypotube is preferably comprised of an elastic material, and more preferably a superelastic material, such as a nickel titanium alloy or other elastic or superelastic metal alloy. The hypotube is cut into a functional design that defines at least three longitudinal segments of respective properties. A distal segment is a highly flexible portion adapted to deflect in any direction across a frontal plane. A central segment is a curvature portion adapted to define a particular curve along its central axis and return to such curvature when deflected along the axis at the front plane. A proximal segment is a mating portion adapted to couple the hypotube relative to the proximal portion of the guiding catheter. A leading arm segment is optionally provided between the curvature segment and the distal segment and is designed to deflect with an intermediate resistance along a single axis of the frontal plane. A support segment is optionally provided between the mating segment and the curvature segment, and is adapted to provide flexural support (resist deflection) when the relatively more distal segments are under load. The various segments are preferably defined with respective patterns cut into the hypotube.

The hypotube is coupled to the braid at a joint using a mechanical interlock that has high torque transfer from the braid to the hypotube. In addition, a short portion of relative higher stiffness polymer tubing (higher than the outer polymer jacket both proximal and distal of the joint) is provided at the joint between the braid and the hypotube. Such higher stiffness polymer tubing redirects force from the joint to the proximal and distal portion of the outer jacket to prevent buckling and kinking of the catheter at the joint.

The outer jacket is heat set over the hypotube. The resin of the jacket is heat set such that at least the axis of the curvature portion of the hypotube extends along a curve, with the inner, exterior, concave surface of the hypotube under compression and the outer, exterior, convex surface (along the apex side) of the hypotube curved under tension. The resin is differentially heat set such that the resin along the inner concave surface is raised to a temperature at or above the melting point of the resin, while the resin at the outer convex surface is raised to a temperature below the melting point of the resin. The resin at the inner concave surface is able to fluidize, relieving residual compressive stress and distributing the resin evenly over the inner, concave surface. The resin at the outer, exterior, convex surface does not melt, preventing exposure of the underlying hypotube, as a resin under tension tends to thin over the upper surface. However, the resin at this outer, exterior surface is permitted to reach a plastic transformation temperature that relieves tensile stress in the material. A system for carrying out the heat setting of the resin onto the hypotube is provided.

BRIEF DESCRIPTION OF THE DRAWINGS

Prior Art

Prior Art

Prior Art

FIG. 7 is third pattern for cutting a hypotube for use in a distal shape-retentive portion of the catheter.

FIG. 10 is a fourth pattern for cutting a hypotube for use in a distal shape-retentive portion of the catheter.

FIG. 13 is a fifth pattern for cutting a hypotube for use in a distal shape-retentive portion of the catheter.

FIG. 29 shows the catheter prior to heat-setting.

FIGS. 30 through 34 show a method of heat-setting the shape-retentive distal end of the catheter.

DETAILED DESCRIPTION OF THE PREFERRED EMBODIMENTS

With reference to the following description, the terms "proximal" and "distal" are defined in reference to the hand of a user of the devices and systems described herein, with the term "proximal" being closer to the user's hand, and the term "distal" being further from the user's hand such as to be often located further within a body of the patient during use.

Figure 1A:
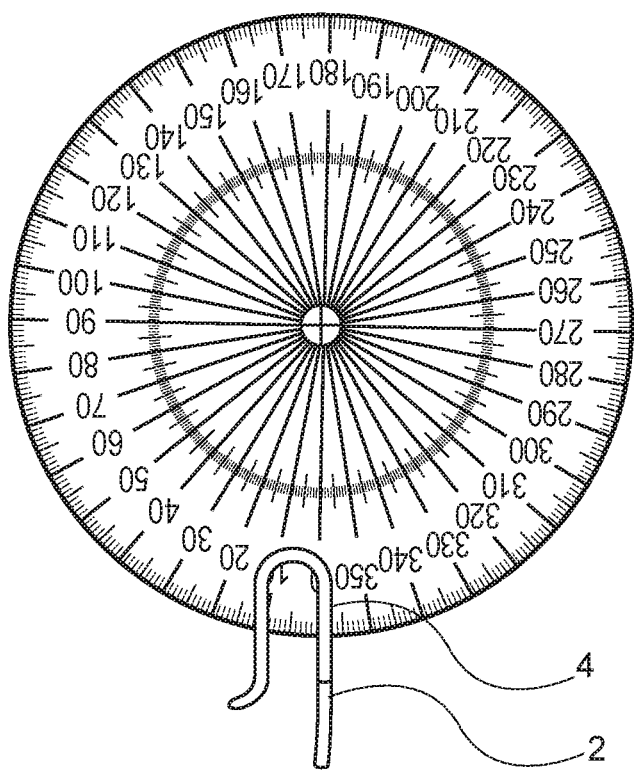
FIG. 1A shows a prior art angiographic catheter in a pre-shaped configuration for use.
Figure 1B:
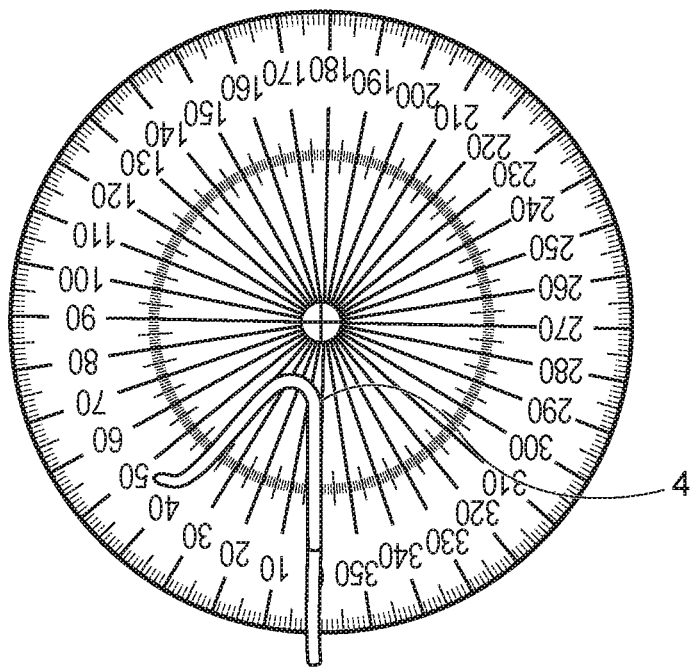
FIG. 1B shows the prior art angiographic catheter deformed from the pre-shaped configuration after being temporarily straightened.
Figure 1C:
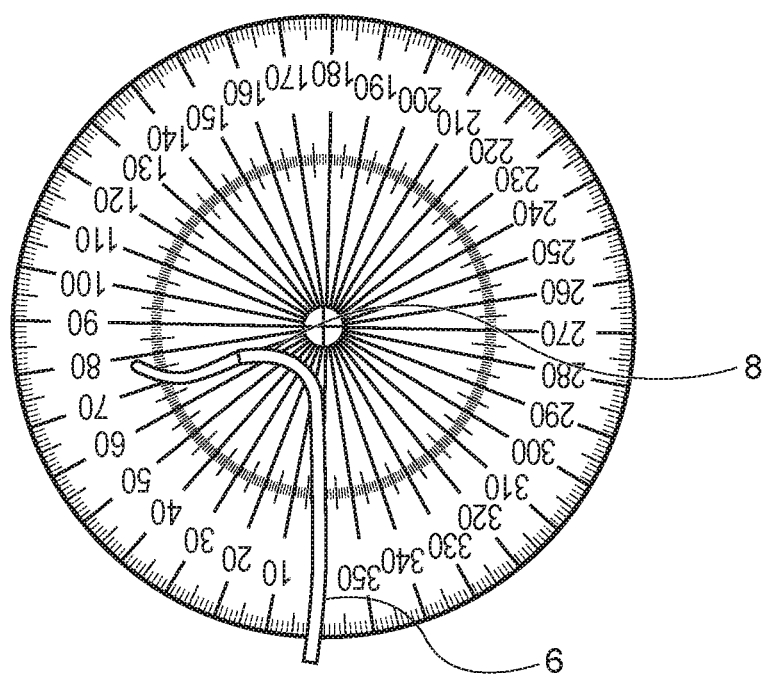
FIG. 1C shows a prior art guiding catheter deformed from its pre-shaped configuration after being temporarily straightened.
Figure 2:
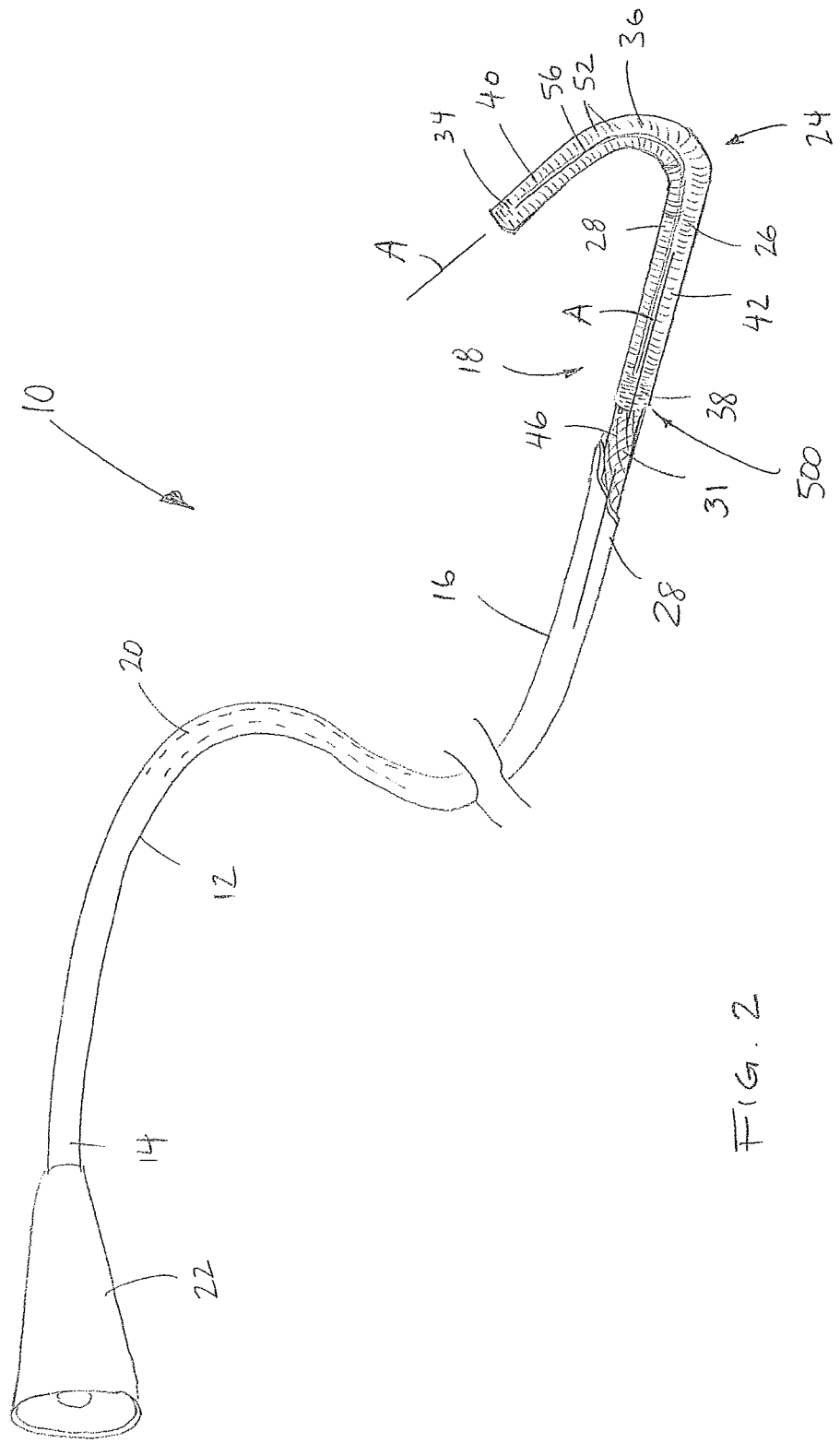
FIG. 2 is a broken partial perspective view of a catheter described herein.

Referring now to FIG. 2, a guiding catheter 10 is shown. The guiding catheter 10 has a proximal portion 12 having a proximal end 14 and a distal portion 16 having a distal end 18, and a lumen 20 and a length extending from the proximal end 14 to the distal end 18. The guide catheter 10 may be provided in different sizes, e.g., 3 French to 7 French for use within different vessels. By way of example, for a 5 French size device, the following dimensions are suitable. The length is generally 65 to 110 cm. The catheter 10 has an outer diameter of 0.066 inch to 0.072 inch, a lumen 20 diameter of 0.054 inch to 0.058 inch, and a wall thickness of 0.004 inch to 0.009 inch between the inner and outer diameters. When the guide catheter is larger or smaller than 5 French, the wall thicknesses and diameters are scaled up or down accordingly, while the length may remain consistent or different as necessary for the procedure. The proximal portion 12 includes a hub 22, optionally with leur lock, to facilitate entry of a secondary instrument into the lumen 20 of the guiding catheter.

The major length of the catheter 10 preferably comprises a tubular braid 46. At the distal end of the tubular braid 46, a distal shape-retentive section 24 is provided. The shape-retentive section 24 comprises a hypotube 26 cut to define particular mating, support, shape-retentive and flexibility characteristics, as described in more detail below. The shape-retentive hypotube 26 is preferably comprised of an elastic material, and more preferably a superelastic material, such as a nickel titanium alloy, stainless steel alloy, or other suitable metal alloy or non-metal material. A polymer tubular liner 31 extends through the braid and hypotube 26, and defines a longitudinal axis A and working lumen of the guiding catheter. The braid 46 and hypotube 26 are also coated in a thermoplastic resin outer jacket 28, as also described in more detail below.

The hypotube 26 defines at least three longitudinal segments of respective properties. In a preferred embodiment, the respective properties are defined by laser cutting a functional design into the hypotube; i.e., a lattice structure including longitudinal spines 56, 58 and relatively perpendicular or transverse struts 52 of defined orientation and width that provide functional characteristics along the length of the hypotube 26. Specifically, a distal segment 34 is highly flexible and adapted to deflect in any direction relative to the longitudinal axis across a frontal plane; a central segment 36 is defines a particular curve and orientation of flexure along its portion of the longitudinal axis and returns to such curvature when the deflection force is removed; and a proximal segment 38 defines mating structure adapted to facilitate coupling the hypotube 26 to the braid 46 of the guiding catheter 10. A leading arm segment 40 is preferably provided between the central curvature segment 36 and the distal highly flexible segment 34 and is designed to deflect with an intermediate resistance along a single axis. A support segment 42 is preferably provided between the central curvature segment 36 and the mating segment 38, and is adapted to provide flexural support (deflection resistance) when the relatively distal segments 34, 36, 42 are under load. The various segments are defined with respective patterns preferably laser cut into the hypotube, although the patterns may be defined via a different method such as, e.g., chemical etching or mechanical cutting. The patterns described in FIGS. 2 through 6 are illustrated as flat projected patterns, but should be visualized as projected 360° about the circumference of the hypotube 26.

Figure 3:
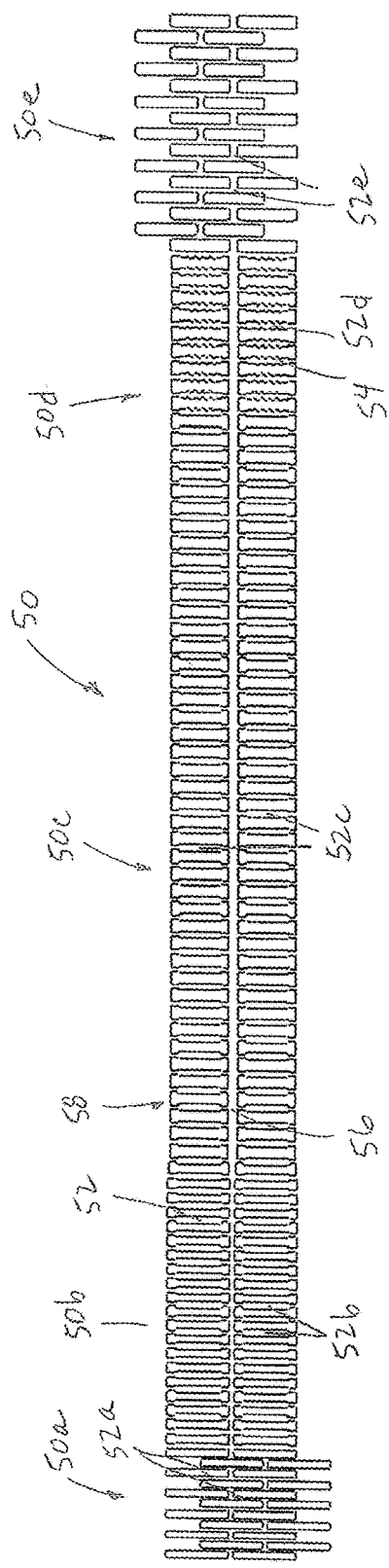
FIG. 3 is a first pattern for cutting a hypotube for use in a distal shape-retentive portion of the catheter.
Figure 4:
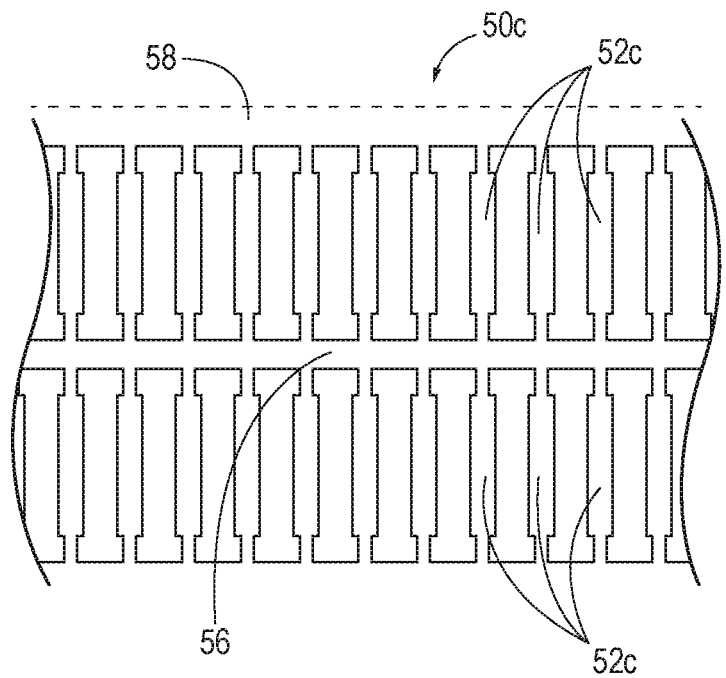
FIG. 4 is an enlarged section of a central curvature portion of the first pattern.
Figure 5:
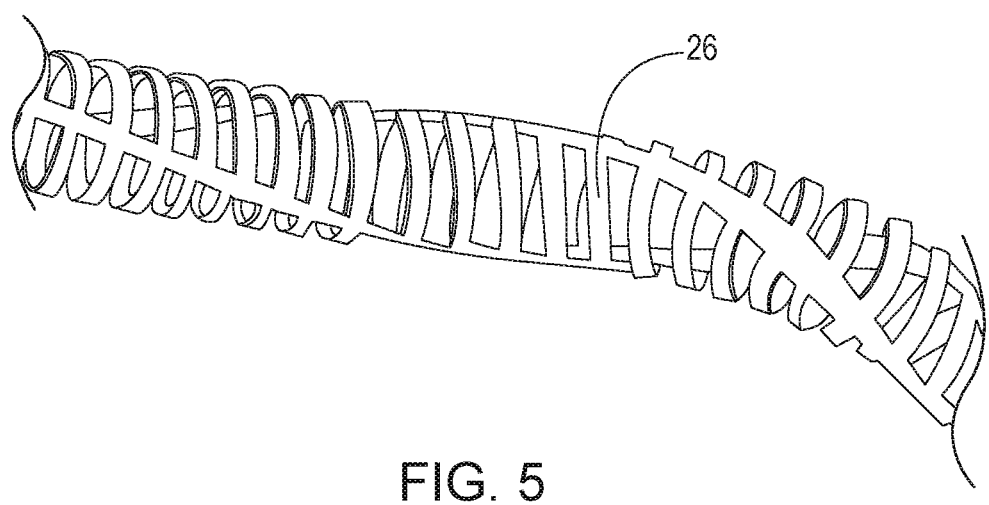
FIG. 5 shows the central curvature portion of the hypotube cut according to the first pattern and subject to torsion.

Turning now to FIG. 3, a first pattern 50 identifies the pattern of areas of material to be removed from the hypotube, such as by laser cutting; i.e., the negative space. The first pattern defines a remainder of positive space in the form of the spines 56, 58 and the struts 52. The spines 56, 58 extend parallel to the longitudinal axis of the hypotube. The struts 52 are longitudinally displaced and laterally extending ribs, all oriented perpendicular to the spines 56, 58. The pattern 50a at the distal segment 34 includes the narrowest struts 52a provided in an offset, or interleaving, pattern. This aids in distal flexibility. The pattern 50c at the curvature segment 36 includes the widest struts 52c. The pattern 50b at the leading arm segment 40 has struts 52b at an intermediate width between the sizes of the struts 52a, 52c of the distal and curvature segments. The pattern 50e at the proximal mating segment 38 is patterned similarly to 50a of the distal segment 34, but has wider struts 52e. The pattern 50d for the support segment 42 defines struts 52d similarly arranged to the curvature segment but at least a portion of the struts preferably have zig-zag edging 54 provided along the long sides of the struts 52d. The zig-zag edging 54 aids in adhesion of the overlying and underlying resin at the support segment 42. One spine 56 is shown along the center of the pattern; the other spine 58 is defined between the opposing ends of the struts as the pattern 50 is projected onto and cut into the hypotube. The two spines 56, 58 extend through the support, curvature and leading arm segments, with the spines 56, 58 widest at the curvature and support segments 36, 42 (e.g., 0.013 inch), and preferably tapering through the leading arm segment 40 (0.0115 to 0.007 inch). The spines do not extend through the patterns 50a, 50e of interleaving struts at the distal and proximal mating segments 34, 38. In accord with the first pattern 50, the struts have a symmetrical structure about the spines such that hemi-tubular portions of the hypotube are the same. FIG. 4 more particularly illustrates the pattern 50c of the curvature segment and FIG. 5 shows a portion of hypotube 26 laser cut with such pattern 50c and its behavior under torsion.

Figure 6:
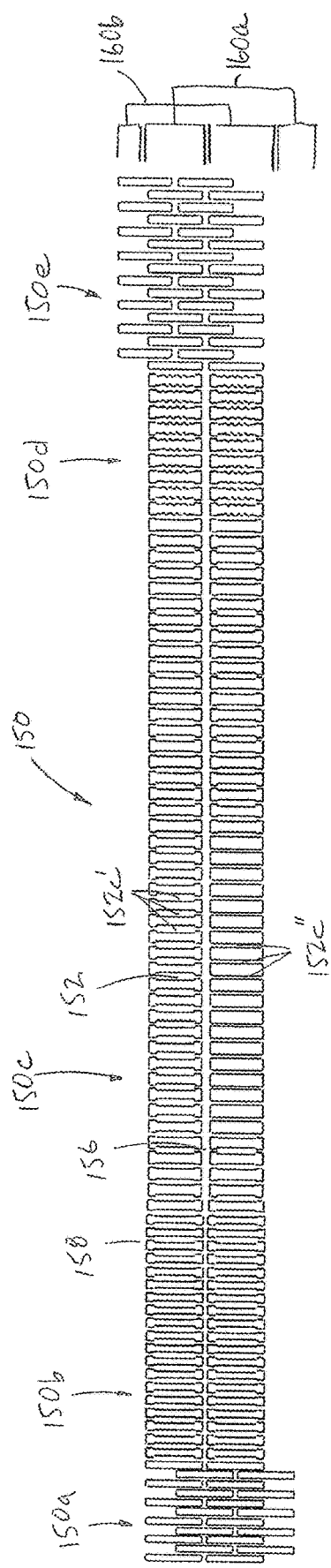
FIG. 6 is a second pattern for cutting a hypotube for use in a distal shape-retentive portion of the catheter.

Turning to FIG. 6, a second pattern 150 includes struts 152 that are all oriented as perpendicular ribs relative to the spines 156, 158, but configured to bias the hypotube in a determined orientation. The patterns for the distal, leading arm, support and proximal mating segments 150a, 150c, 150d, 150e, as well as the spine dimensions, are preferably the same or substantially similar to that described in the first pattern 50. The curvature segment 150b includes asymmetric central struts 152b', 152", in which one hemi-tubular portion 160a has wider struts and its opposite hemi-tubular portion 160b has narrower struts, thereby providing an inherent bias to deflection and bending toward the hemi-tubular portion 160b.

Figure 8:
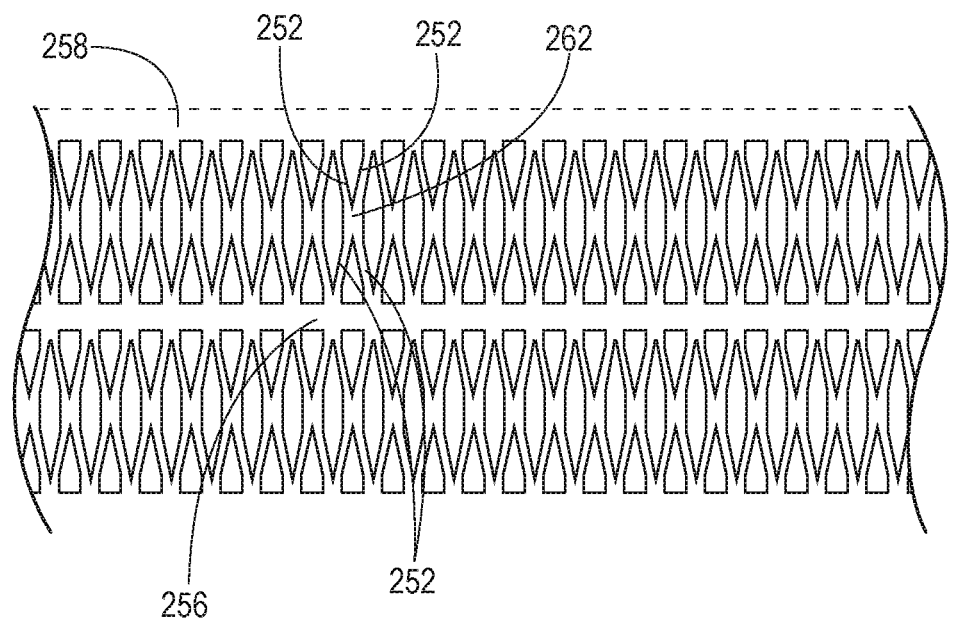
FIG. 8 is an enlarged section of a central curvature portion of the third pattern.
Figure 9:
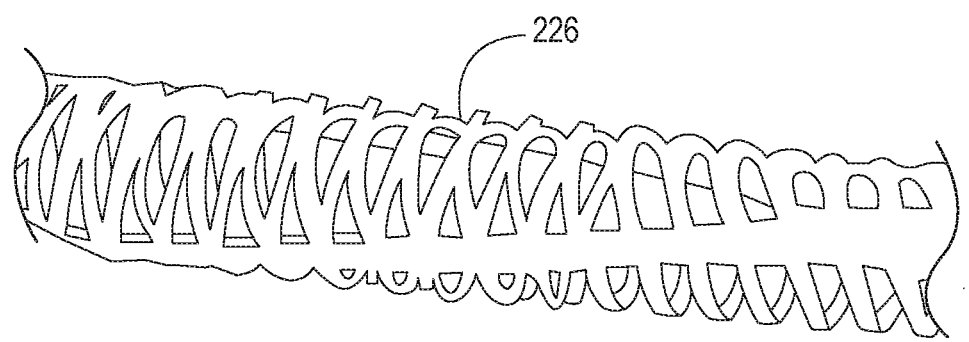
FIG. 9 shows the central curvature portion of the hypotube cut according to the third pattern and subject to torsion.

Referring to FIG. 7, a third pattern 250 includes distal and proximal mating segments 250a, 250e and spine configurations that are substantially as described, as in the first pattern 50. However, the struts 252 at the leading arm, curvature and support segments 250b, 250c, 250d are angled relative to the spines 256, 258 in a lattice arrangement. Specifically, referring to FIG. 8, the lattice pattern of the struts 252 is defined by interlocked struts extending in X-shaped arrangements between the spines 256, 258, with the struts meeting at joints 262 laterally between the spines. In pattern 250, struts 252 are preferably widest at the curvature and support segments 250c, 250d and reduced in width toward and through the leading arm segment 250b. FIG. 9 illustrates a portion of the hypotube 226 formed by the laser cut pattern 250 for the lattice arrangement in FIG. 8.

Figure 11:
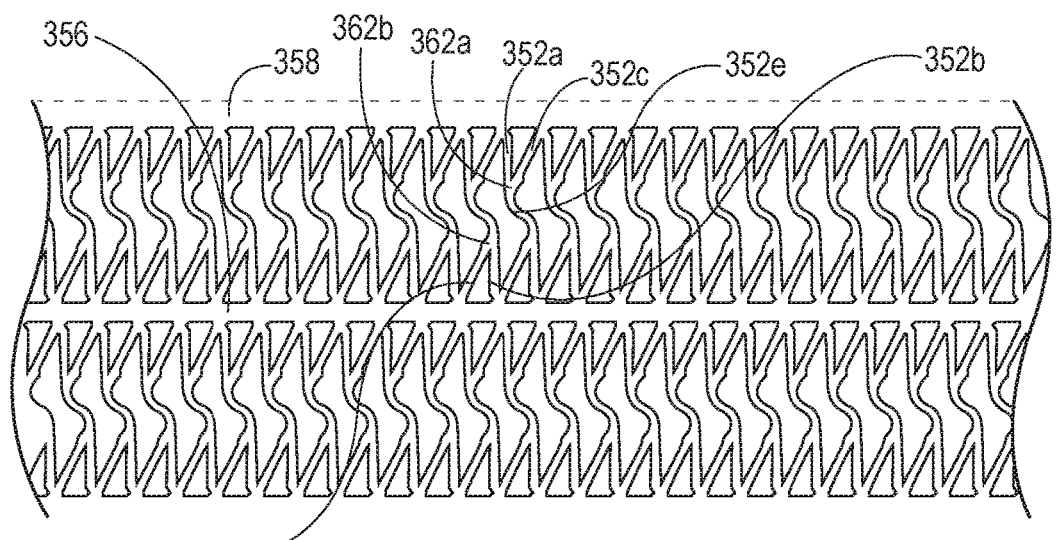
FIG. 11 is an enlarged section of a central curvature portion of the fourth pattern.
Figure 12:
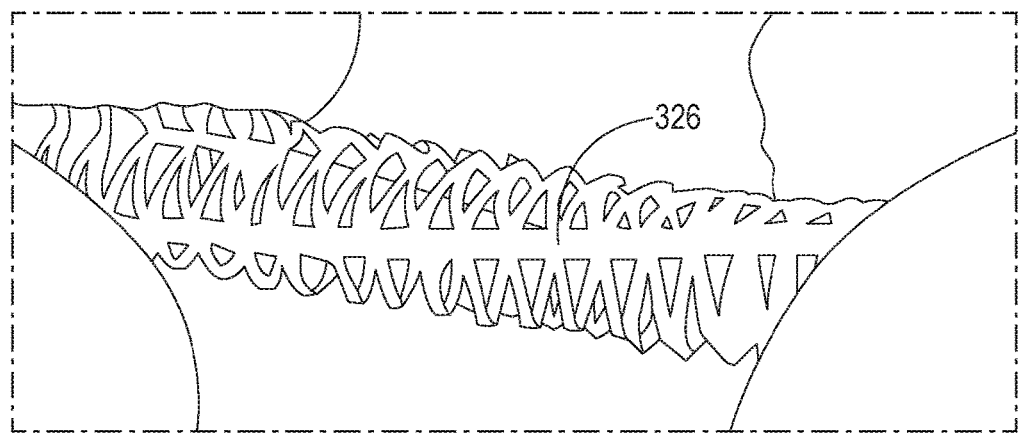
FIG. 12 shows the central curvature portion of the hypotube cut according to the fourth pattern and subject to torsion.

Turning to FIG. 10, a fourth pattern 350 includes distal and proximal mating segments 350a, 350e and spine configurations that are substantially as described as in the first pattern 50. The struts 352 at the leading arm, curvature and support segments 350b, 350c, 350d are provided in a lattice arrangement, which is generally wavy. Referring to FIG. 11, the wavy lattice arrangement may be a pattern of longitudinally offset first and second struts 352a, 352b that extend perpendicularly from opposing spines 356, 358, third and fourth struts 352c, 352d that extend parallel to each other and at an angle to the first and second struts, with the first and third and second and fourth struts meeting at respective first and second joints 362a, 362b, and a fifth strut 352e that couples the first and second joints, the fifth strut transversely oriented relative to the first, second, third and fourth struts, and generally perpendicular to the second and fourth struts. FIG. 12 illustrates a portion of the hypotube 326 formed by the laser cut pattern 350 of the lattice arrangement in FIG. 11. The struts in such wavy lattice may have different sizes in different segments or in different portions of a same segment. In the fourth pattern 350, the struts in the curvature segment 350c and support segment 350d are preferably larger than the struts in the leading arm segment 350b. The struts in the wavy pattern transfer force applied to the hypotube at an angle so that the spine deflects in torsion.

Figure 14:
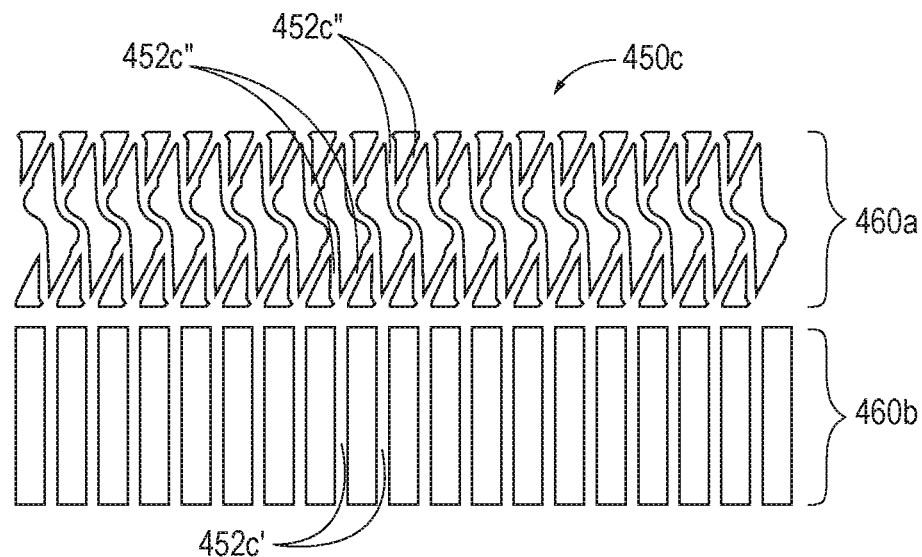
FIG. 14 is an enlarged section of a central curvature portion of the fifth pattern.
Figure 15:
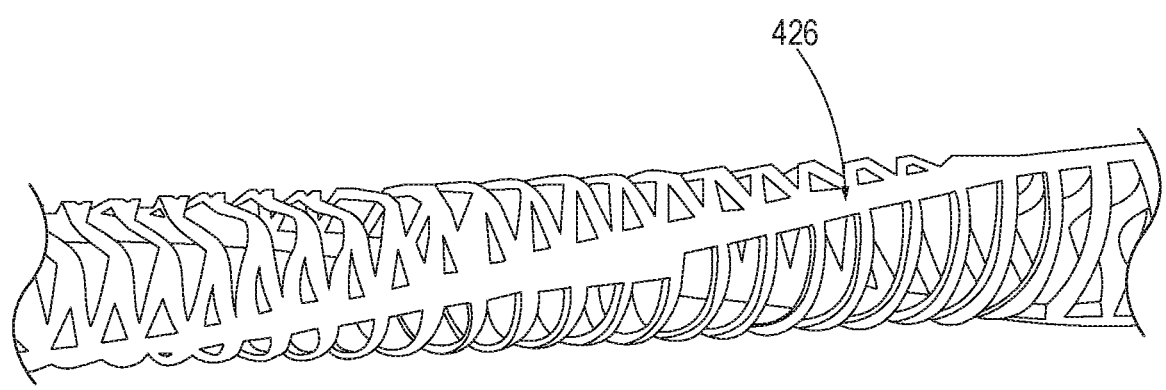
FIG. 15 shows the central curvature portion of the hypotube cut according to the fifth pattern and subject to torsion.

Referring now to FIG. 13, a fifth pattern 450 is a hybrid design having portions with both struts in a wavy lattice and struts in a perpendicular rib-like arrangement. The fifth pattern 450 includes distal and proximal mating segments 450a, 450e and spine configurations that are substantially as described as in the first pattern. The struts in the support segment 450d are oriented perpendicular to the spines 456, 458. The support segment 450d includes a proximal portion 450d' with struts 452d' having zig-zag edges, and a distal portion 450d" with struts 452d" having straight edges. The leading arm segment 450b has struts 452b of preferably uniform width also extending perpendicularly relative to the spines 456, 458 but smaller than those in the support segment 450d. As shown in FIG. 14, the pattern for the curvature segment 450c defines, at a first hemi-tubular portion 460a, rib-like struts 452c' of preferably uniform width, though smaller than the struts of the support segment 450d, extending perpendicular to the spines 456, 458 and, at a second opposing hemi-tubular portion 460b, struts 452c" in a wavy configuration as described above with respect to the fourth pattern 350. Also, the struts may be larger at a proximal end of the curvature segment 450c than at the distal end thereof. FIG. 15 illustrates a curvature segment 450c of a hypotube 426 formed by the laser cut pattern 450 shown in FIG. 14 and subject to torsion.

Figure 16:
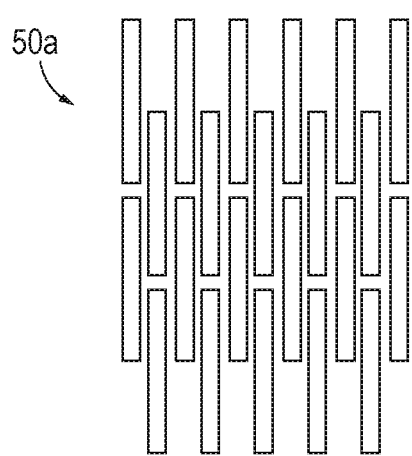
FIG. 16 is an enlarged section of a pattern for cutting the distal segment of the hypotube.
Figure 17:
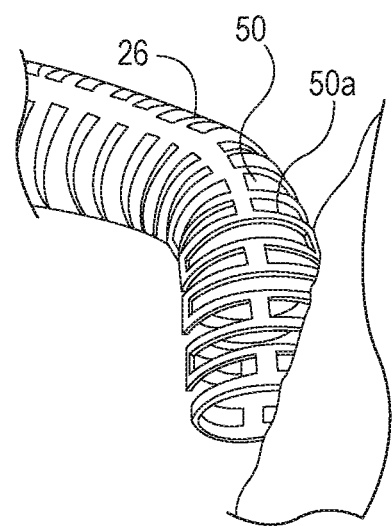
FIG. 17 shows the flexibility of the distal segment of the hypotube cut according to the first through fifth patterns.
Figure 18:
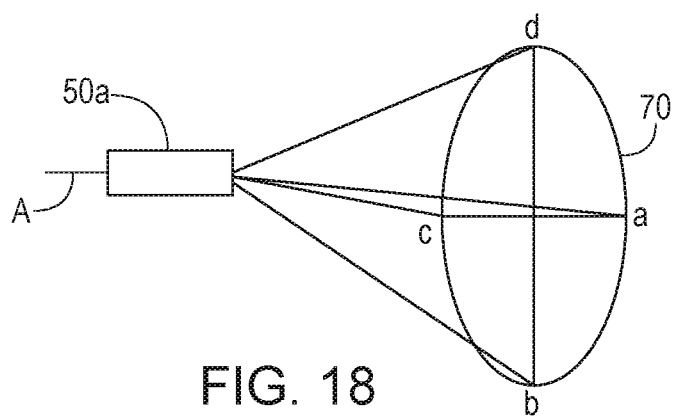
FIG. 18 illustrates the flexibility of the distal segment of the hypotube cut according to the patterns.

Turning now to FIGS. 16 and 17, with respect to each of the patterns 50, 150, 250, 350, 450, the distal segment (e.g., 50a) is structurally adapted for flexibility to allow the device to freely track over a guidewire and provides a flexible atraumatic tip at the distal end of the catheter 10. The cut pattern defines a deflection plane 70 that is equally able to be deflected in any of directions a, b, c, d (90° apart), or in intermediate directions, relative to the longitudinal axis A (FIG. 18). The laser cut pattern provides both positive and negative space within the hypotube 26 to allow for the resin of the outer jacket 28 to evenly fill the negative space and provide adhesion between the positive space and the underlying liner 31 (FIG. 2). Specifically, the widths of defined struts in the distal segment 50a of the hypotube are designed to allow the outer jacket resin to wick under the hypotube 26 during the resin-coating process, described below, which also results in the hypotube adhering to the liner 31 and forming a cohesive device. Further, the spacing of the struts from each other is designed to provide support to the distal segment during pressurization.

The leading arm segment 50b, 150b, 250b, 350b, 450b, is adapted to deflect with intermediate resistance (i.e., less than the distal segment) along a single axis of a frontal plane. The deflection plane is defined between the two spines, e.g., 56, 58. The width of the spines 56, 58 governs resistance to deflection along the frontal plane and retention of the set shape after deflection. The spines 56, 58 may or may not provide flexural support. In patterns where the spines do not provide flexural support (e.g., patterns 50 and 150), the thickness of the wall of the hypotube relative to the width of the spines should remain within a 1:4 to 1:3 ratio in order to maximize spring force while preventing buckling. The use of interconnected struts (e.g., as shown in patterns 250, 350 and 450) can provide additional force used to add deflection resistance and shape retention. In such cases, adequate retention force can be supplied using members with 1:1 tube thickness/support width ratios. In general, the width of the spines is a primary factor governing the resistance to deflection and shape retention, while the thickness of the spines is a determining characteristic in the stability of the hypotube (resistance to buckling). A design with a 1:1 ratio of the hypotube wall thickness to spine width will be more dimensionally stable, but will not supply as much force as a design with a 1:2 or 1:3 ratio. The optimal hypotube wall thickness to spine width ratio is also dependent upon the radius of curvature. In an exemplar device comprising a hypotube with a 0.060 inch inner diameter and a 0.067 inch outer diameter (defining a 0.0035 inch wall thickness), adequate resistance to deflection and good shape retention were obtained on a 10 mm diameter curvature using 0.0135 inch wide spines and struts in a rib pattern (patterns 50 and 150). As the curvature diameter increases, the wall thickness to spine width ratio can decrease to 1:5, 1:6 or even less without resulting in buckling of the structure. In an alternative design using identical tube geometry, the same deflection resistance and shape retention can be achieved using an interlocked lattice pattern where the wall tube thickness is 0.0035 inch, the spine width is 0.010 inch, and the interlocking lattice elements are 0.002 inch to 0.006 inch in width (patterns 250 and 350).

Figure 19:
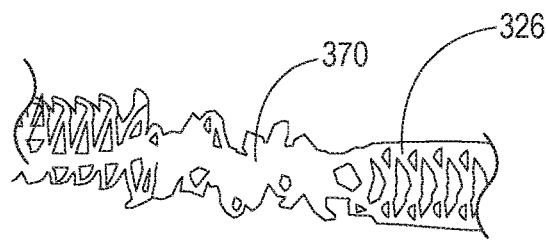
FIGS. 19 and 20 illustrate the function of spine elements in the hypotube when subject to torsion and recovery from torsion.
Figure 20:
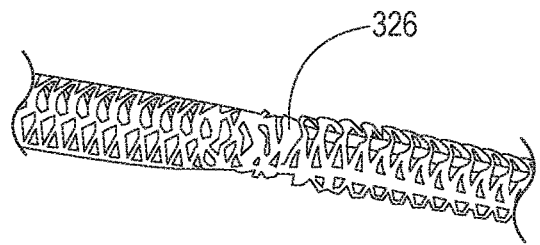

The leading segment 50b, 150b, 250b, 350b, 450b is also designed to deflect along the central axis A (FIG. 2) under a torsional force. Such deflection makes the leading segment atraumatic during tracking and positioning within a vessel. Deflection causes the torsional force to transfer into the hypotube by distorting supporting structures and allowing the spines to close in and wrap around each other. In patterns designed to minimize deflection under torque, force is transferred in plane around the radial axis. This builds up high amounts of stress until local buckling of the structure occurs, shearing through the tube and causing separation. In distinction, the hypotube at the leading segment when subject to torsion is preferably designed to allow the spines to fold over each other to the point of lumen collapse (at 370) (FIG. 19), preventing separation of the hypotube from the remainder of the catheter. The superelastic characteristic of the hypotube 326 allows the hypotube to return to shape once the torsion is removed (FIG. 20).

The curvature segment is structured to retain its shape when deflected along the central axis A through the frontal plane. The spines 56, 58 of the hypotube 26 determine the direction of deflection, with deflection occurring between the spines. The widths of the spines 56, 58 govern resistance to deflection and assist in retention of the set shape after deflection. As described above with respect to the leading arm segment, the curvature segment is adapted to deflect along central axis A when subject to torsional force. Such deflection makes the curvature segment atraumatic during tracking and positioning. The curvature segment is also structured to allow the spines 56, 58 to fold over each other at point of lumen collapse under torsion, preventing separation of the hypotube. This ability to deflect and fold allows the curvature segment to withstand torsional force without separation from the remainder of the catheter.

Figure 38:
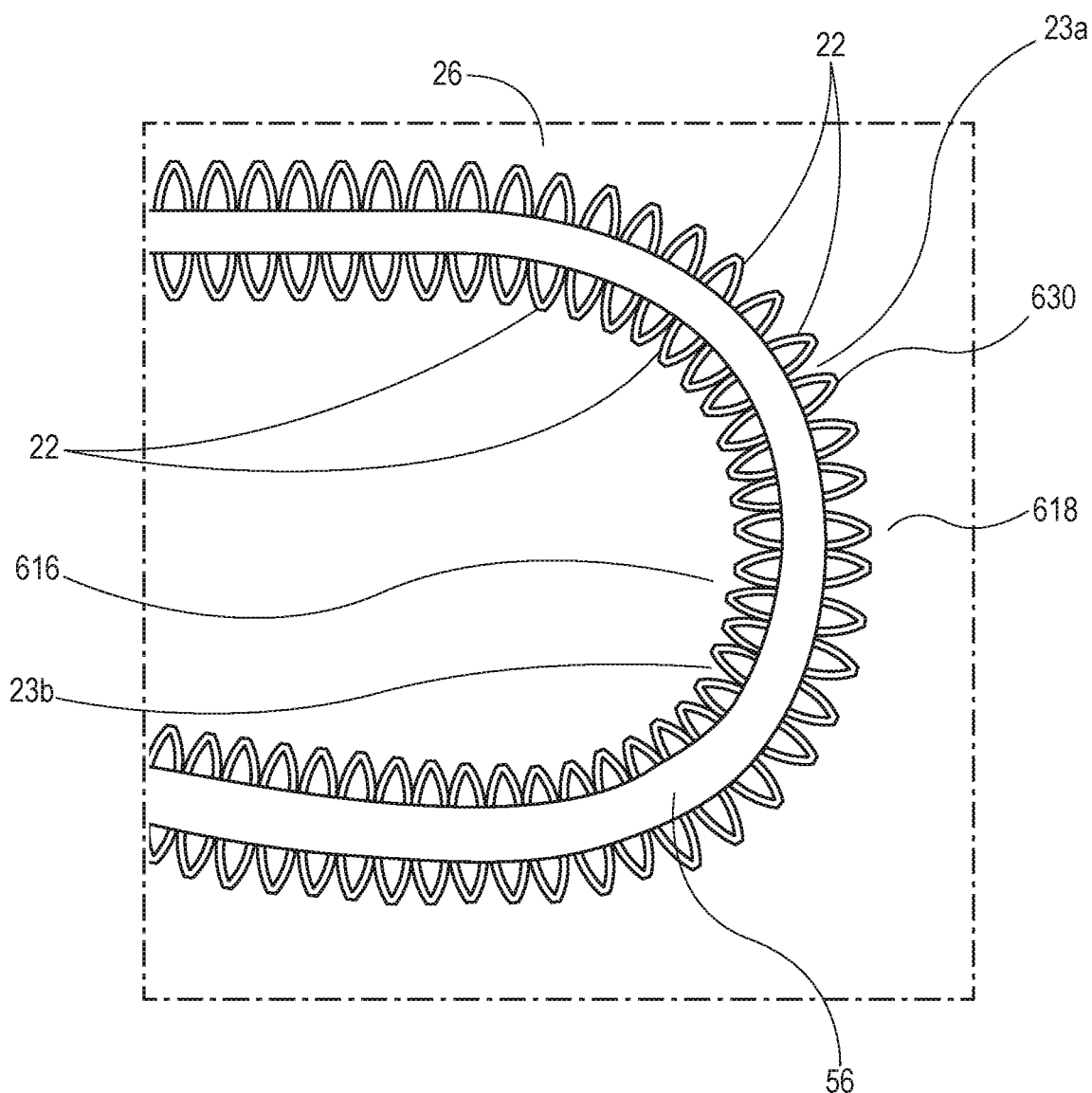
FIG. 38 is an enlarged view showing features of a curvature segment of the hypotube.

Further, turning to FIG. 38, the curvature segment is preferably designed to have an interlocked pattern of struts 22 on the apex 618 of curvature to support resin (not shown). The interlocked pattern may comprise a braced X-shaped arrangement 630 of the struts extending between the spines 56 (, 58). As the hypotube 26 is shaped into its curved form, the spacings 23a between the struts 22 on the apex 618 of curvature widen while the spacings 23b at the underside 616 of the curvature relatively narrow. The spacing between the struts needs to be controlled in order to withstand adequate burst pressure, bearing in mind that guide catheters are used to infuse contrast, sometimes under significant pressure in order to fully visualize the anatomy. In a typical construction in which the overall catheter wall thickness is 0.007" and the resin is composed of a low durometer, relatively weak material, an acceptable range for the gap between the strut elements is 0.001 inch to 0.020 inch. While this gap range can be maintained in some cases by increasing the frequency of overlying features, there is a practical design limit at which distortion due to curvature prevents appropriate coverage of supporting metal elements. One solution is with an interlocked pattern, such as shown in patterns 250, 350, 450 in which at the respective curvature segments 250c, 350c, 450c no single strut is separated from another strut by more than a maximum determined gap size. While individual struts stretch and spread, adequate overall coverage is maintained.

A similar effect can be achieved by biasing the ratio of cut and uncut material so that more hypotube material is preserved on the apex of the curvature segment 150c than on the underside (FIG. 6). In one example, the hypotube includes 0.012-inch-wide rib-like struts on the outer, exterior, convex (upper or apical) surface and 0.009 inch ribs on the inner, exterior, concave (lower) surface. If the struts are spaced at 0.0025 inch intervals with a narrow connection point as is shown in the rib design, the gap between ribs on the upper surface would be approximately 0.013 inch and the gap between ribs on the lower surface would be approximately 0.016 inch. When the device is curved, the gap on the upper surface widens and that on the lower surface reduces, resulting in a final device where gaps on both the upper and under surfaces are approximately 0.014 inch.

As shown in patterns 150 and 450, the curvature segment 150c, 450c may also be designed to have a higher cut to uncut ratio for the hypotube such that less hypotube material remains at the lower surface. This feature may also be provided to modified patterns 250 and 350, to provide lattice structures for the struts that are thicker on the apical upper surface and thinner on the lower surface. This promotes even resin filling when the curvature segment is curved.

The support segment (e.g., 50d) has similar structural and functional characteristics to the curvature segment, but may optionally have a pattern adapted to increase its mechanical interlock with resins to enhance bond force at a joint 500 between the hypotube 26 and the braid 46. Specifically, the support segment includes the same structures that provide the above-described ability to deflect and fold and which thereby allow the hypotube to withstand torsional force without separation from the remainder of the catheter. Thus, it is appreciated that when a sufficient torsion is applied over proximal and distal portions of the hypotube, the hypotube deflects and folds, and then returns to shape once the torsional force is removed.

Figure 21:
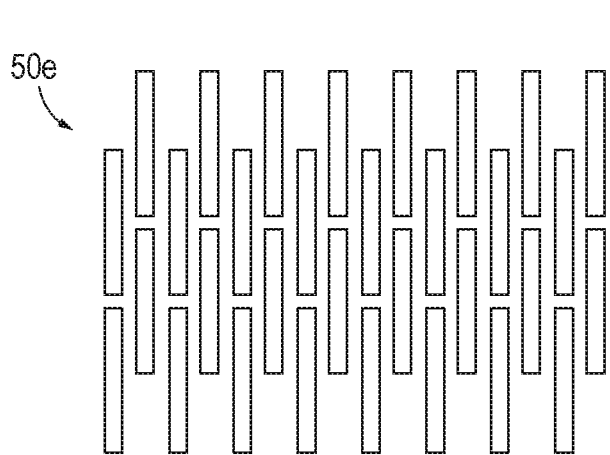
FIG. 21 is an enlarged section of a pattern for cutting the proximal segment of the hypotube.
Figure 22:
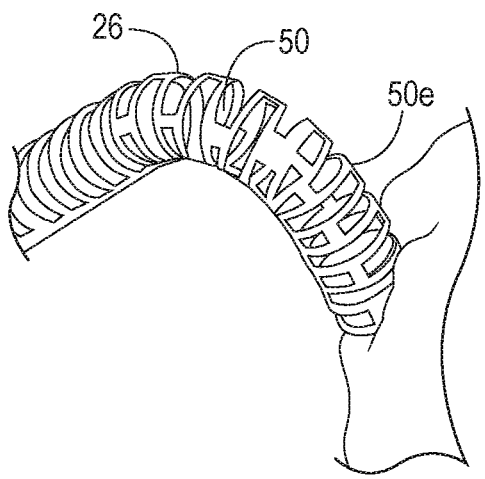
FIG. 22 shows the flexibility of the proximal segment of the hypotube cut according to the first through fifth patterns.

Turning to FIGS. 21 and 22, the proximal mating segment 38 of the hypotube 26 is adapted to mimic the stiffness, axial flexibility and kink performance of the proximal braid 46 of the catheter. This allows the proximal mating segment 38 to transition from the relatively distal segments of the hypotube 26 to the remainder of the catheter. The proximal mating segment 38 is designed to allow a high torque transfer from the relatively proximal braid to the hypotube, as well as prevent buckling and provide kink resistance. To do so the catheter (1) has reinforcing materials on either side of the joint 500 between the hypotube 26 and braided portion 46 with similar mechanical behavior (kink radius, column strength, deflection resistance, torque transfer); (2) has a joint 500 comprised of three interdependent segments with a defined kink radius and deflection force specification; (3) defines a minimum separation gap between the reinforcing materials; (4) has a joint with a rotational interlock between the braid and hypotube; and preferably (5) utilizes continuous high strength polymeric material for each of the inner liner 31 through the braid and hypotube, and the outer jacket 28 over the braid and hypotube.

Figure 39A:
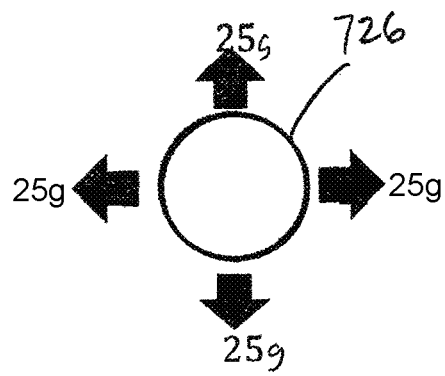
FIG. 39A illustrates the force to deflect a hypotube with an unbiased pattern of struts.
Figure 42:
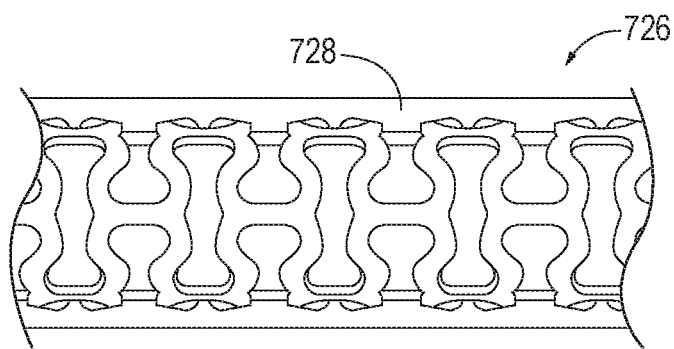
FIG. 42 is a portion of an unbiased hypotube for a guiding catheter.
Figure 43:
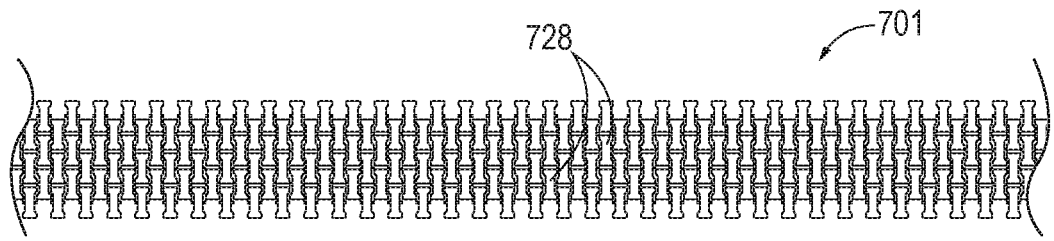
FIG. 43 illustrates a pattern for cutting the portion of the hypotube shown in FIG. 42.

Referring to FIG. 39A, in one manufactured form, the hypotube 726 requires equal force to be bent in any direction. For example, 25 grams of force may be required to push the hypotube in each of four directions. Such a hypotube manufacture is shown in FIG. 42, which has a strut layout generated from the laser cut pattern 701 of FIG. 43. The pattern creates a longitudinally repeated offset pattern of a plurality of, e.g. three, 'dogbone'-shaped openings 728 circumferentially cut in the hypotube 726.

Figure 39B:
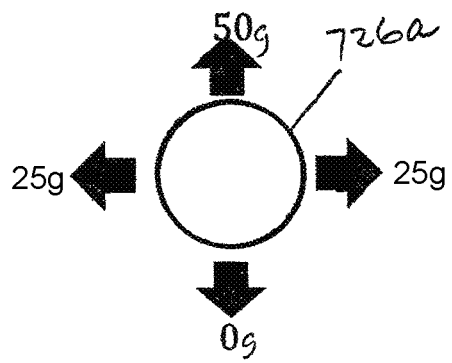
FIG. 39B illustrates the force to deflect a hypotube with an unbiased pattern of struts that has preferential bending along a heat-set axis.

However, turning now to FIG. 39B, the hypotube 726a of FIG. 39A and FIG. 42 can be biased to adopt a curved configuration. The curve can be effected by altering the crystal structure of the superelastic alloy of the hypotube (heat setting the alloy), distorting an unbiased pattern to adopt a curved configuration. This increases resistance to bending counter to the curved configuration and reduces resistance when bending with the curved configuration, as illustrated by the 50 grams of force required to push the hypotube in a first direction and a zero grams of force required to push the hypotube in an opposite second direction.

An unbiased configuration of the hypotube allows the orientation of the hypotube (as part of the guiding catheter) to autocorrect and self-orient if (1) the bending resistance in the plane is adjusted by heat setting and (2) if the laser cut structure allows the hypotube to be torqued along its axis. The resistance to torque or rotate the tube should be less over the portion of the hypotube that is curved than the force required to bend the tube counter to the heat set shape. That is, for autocorrection during guiding through the vessels, the hypotube should be heat set such that its longitudinal axis extends along a curved shape, with the hypotube possessing a rotational stiffness such that the force required to torque the hypotube 180 degrees in rotation is less than the resistance required to bend the hypotube counter to the curved shape. For example, if the resistance to bending a 1 cm long curve is 50 grams, the resistance for torqueing the tube 180 degrees over the tube length should be less than 50 grams.

Figure 40A:
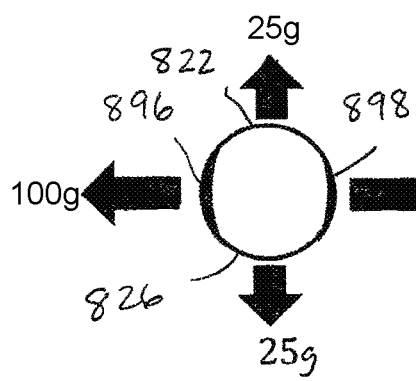
FIG. 40A illustrates the force to deflect a hypotube with parallel spines that alter force deflection.
Figure 40B:
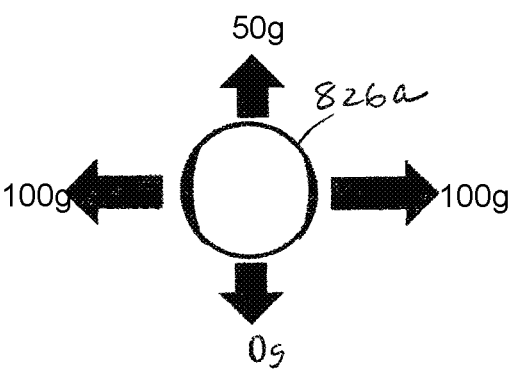
FIG. 40B illustrates the force to deflect a hypotube with parallel spines that alter force deflection and which also has preferential bending along a heat-set axis.

Turning now to FIG. 40A, by placing stiffening spines or struts 896 and 898 along the circumference of a hypotube 826, the hypotube 826 can be constructed to limit bending within a single plane. Referring to FIG. 40B, additionally heat-altering the crystal structure of the superelastic alloy of the hypotube 826a (heat setting the alloy), a biased pattern can be made to adopt a curved configuration. This increases resistance bending counter to the curved configuration and reduces resistance when bending with the curved configuration.

Figure 41A:
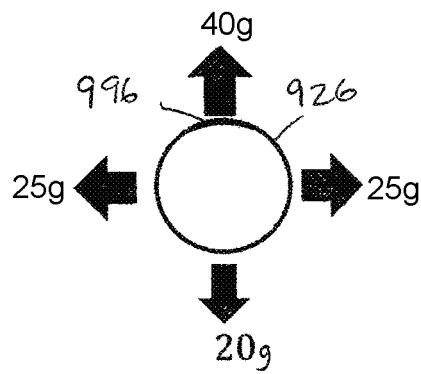
FIG. 41A illustrates the force to deflect a hypotube with a biased pattern of struts.
Figure 41B:
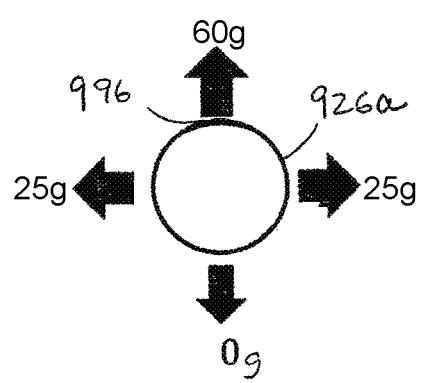
FIG. 41B illustrates the force to deflect a hypotube with a biased pattern of struts that has preferential bending along a heat-set axis.
Figure 44:
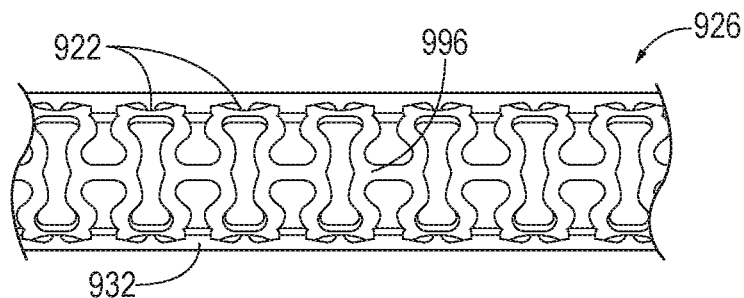
FIG. 44 is a portion of a biased hypotube for a guiding catheter.
Figure 45:
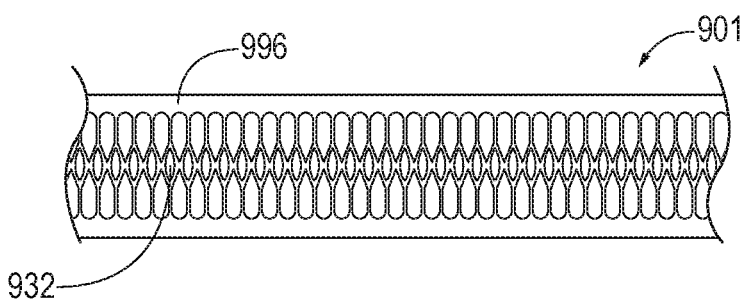
FIG. 45 illustrates a pattern for cutting the portion of the hypotube shown in FIG. 44.

Moreover, referring to FIG. 41A, a hypotube 926 can be constructed with stiffening spine 996 at a single side, requiring additional force to bend in a first direction (e.g., 40 g) relative to its opposite second direction (e.g., 20 g). FIG. 44 shows a portion of the hypotube 926 having a spine 996 with high resistance to bending at one side, and a circumferentially opposing window 932 with low resistance to bending. FIG. 45 illustrates the laser cut pattern 901 for generating the hypotube 926 of FIG. 44. Thus, when the hypotube 926 tracking over a curved anatomical feature, the hypotube bends readily only in the axis parallel to supporting transverse struts 922. This is because the resistance to bending perpendicular to the stiffening spine 996 is greater than bending parallel to the stiffening struts 922, thus locally increasing bending resistance in the direction of the stiffening segment. Then, as shown in FIG. 41B, the hypotube 926a can be biased with heat setting to further prefer bending to one side (60 g relative to zero grams).

Now referring back to FIG. 2, one aspect of the joint 500 between the hypotube 26 and the braid 46 includes matching properties between the hypotube and the braid. For example, for a braided catheter shaft with a kink radius of 3 mm with a flexural modulus of 10 g/cm², the proximal mating segment of the hypotube matches these properties for a minimum of 3 mm in order to form an interface that closely matches that of the braid. It should be understood that the braid and hypotube pattern can be adjusted to produce specified device properties in a controlled and predictable manner.

Figure 23:
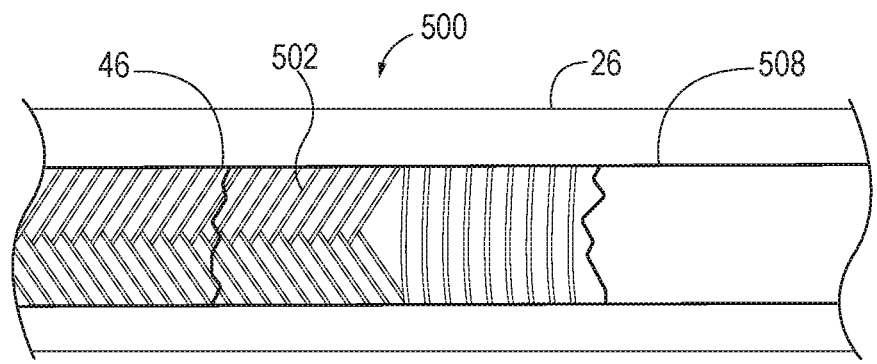
FIG. 23 shows the butt joint between the braid and the distal shape retentive section of the catheter.
Figure 24:
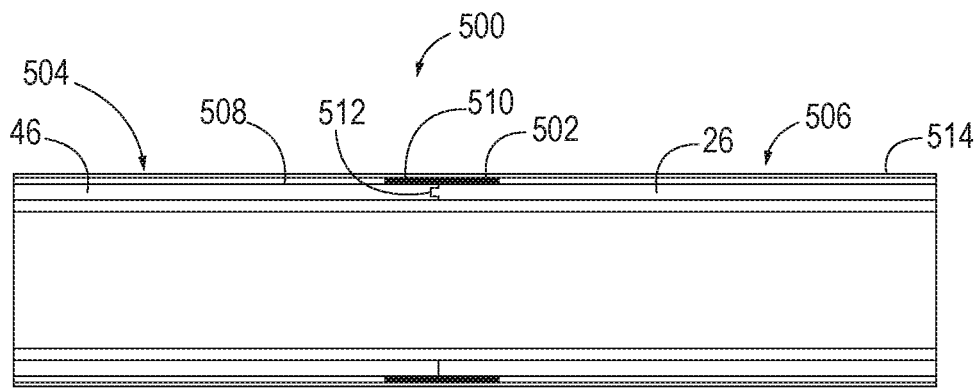
FIG. 24 is a longitudinal section view of the distal end of the catheter, including the butt joint of FIG. 23.
Figure 26:
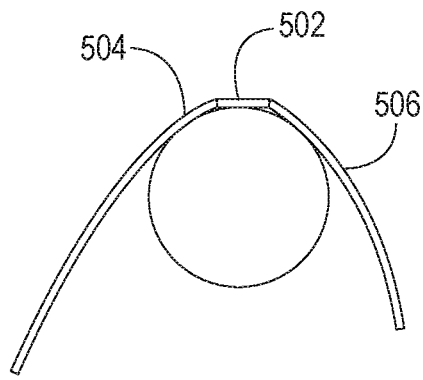
FIG. 26 illustrates the kink resistance of the catheter at the butt joint.

Referring to FIGS. 23 and 24, the joint 500 comprises three longitudinally arranged and interdependent joint segments that together provide kink resistance. In order to achieve the high kink resistance, a central joint segment 502 preferably has a length corresponding to a target minimum kink radius, e.g., 3 mm. The proximal and distal joint segments 504, 506, immediately proximal and distal to the joint 500, preferably have a kink radius one-half to two-thirds of the target radius with a flexural modulus one-half to two-thirds that of the central segment. During bending centered at the joint 500, the proximal and distal segments 504, 506 undergo high deformation while the central segment 502 remains more rigid. Force is deflected away from the central joint 502 as the proximal and distal segments 504, 506 bend, but do not kink within the specified target kink radius (FIG. 26).

In one embodiment of the catheter, these properties of the joint 500 are achieved by varying the durometer of the elastomeric resin forming the outer jacket 28 over the hypotube 26 and braid 46. The proximal and distal joint segments 504, 506 are jacketed in a low durometer resin (60A to 55D durometer), while the central joint segment 502 is jacketed in a higher durometer resin (typically 10 to 60 durometer higher than proximal and distal segments). The selective stiffening of the central joint segment 502 with a higher durometer resin results in a higher flexural modulus than the proximal and distal joint segments 504, 506. The length of the central joint segment 502 and the difference in durometer between the resin utilized for the central segment 502 in relation to the proximal and distal segments 504, 506 is then adjusted to achieve the preferred properties.

The central joint segment 502 may be reinforced with a high stiffness adhesive over a defined length. The joint is then covered in an elastomeric resin tube or wrap 508. The stiffness and length of adhesive jacket application can then be adjusted to achieve the preferred properties.

In another embodiment of the device, a thin high durometer tubular extrusion or wrap such as polytetrafluoroethylene (PTFE), fluorinated ethylene propylene (FEP), perfluoroalkoxy (PFA), ethylene tetrafluoroethylene (ETFE), polyethylene terephthalate (PET), and/or polyetheretherketone (PEEK) polymers can additionally or alternatively be placed over the central joint segment 502 prior to jacketing with an elastomeric resin. The length, durometer, and thickness of this extrusion or wrap can be adjusted to achieve the properties described above.

Figure 25:
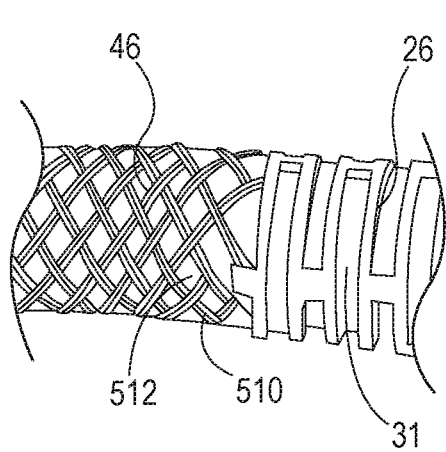
FIG. 25 shows the interlock between a tab at the proximal end of the hypotube and the braid.

In order to minimize the separation gap between the hypotube 26 and the braid 46, which would function as a mechanical discontinuity, one or more interlocking elements 510 extend from the hypotube into spaces 512 defined at the ends of the braid 46 (FIG. 25). The one or more interlocking elements 510 interlock with the braid 46 at the spaces 512 to transfer torque through the joint 500. In one embodiment, the interlocking elements are tabs machined or laser cut from the hypotube to closely fit within spaces formed at the end of the abutting braid. These space 512 can be defined by the extension of the braid wires. The geometry of the tabs 510 should fall within the spacing of the braid wire to prevent the hypotube 26 and braid 46 from overlapping. The outer jacket 508 extends over the joint 500, constraining movement during applied torsion. The tabs 510 interlock with the end of the braid 46, allowing the mechanical transfer of torque from the braid 46, across the joint 500, and to the hypotube 26.

The continuous high strength polymeric materials used at the inner lining 31 and outer jacket 508 reinforces the joint 500 and allows for acceptable tensile strength and torque transfer properties. The thickness of the inner lining 31 and/or outer jacket 508 is determined by the intended kink resistance, flexibility, and tensile strength of the device. The material is designed to minimize thickness (and thereby minimize impact to kink resistance and flexibility of the device) to achieve the required tensile strength. In one embodiment, a thin continuous extrusion of PTFE ranging between 0.00025 inch and 0.003 inch in thickness and most preferably between 0.0005 inch and 0.0015 inch in thickness is applied to the inner lumen of the device and defines the inner lining 31. The braid 46 and hypotube 26 are positioned as described above over this inner liner 31. The outer jacket 508 of thermoplastic elastomeric material is then positioned over the braid 46 and hypotube 26 and heated to join with the braid 46, hypotube 26, and PTFE liner 31. A second continuous layer 514 of high strength material such as PET is then preferably applied to the outer jacket 28 of the device. The thickness of the second layer 514 ranges between 0.0001 inch and 0.003 inch and most preferably ranges from 0.00025 inch to 0.00075 inch in thickness. The resulting device can achieve a kink resistance of 8 mm or less and has a tensile strength of over 8 lb·f.

Figure 35:
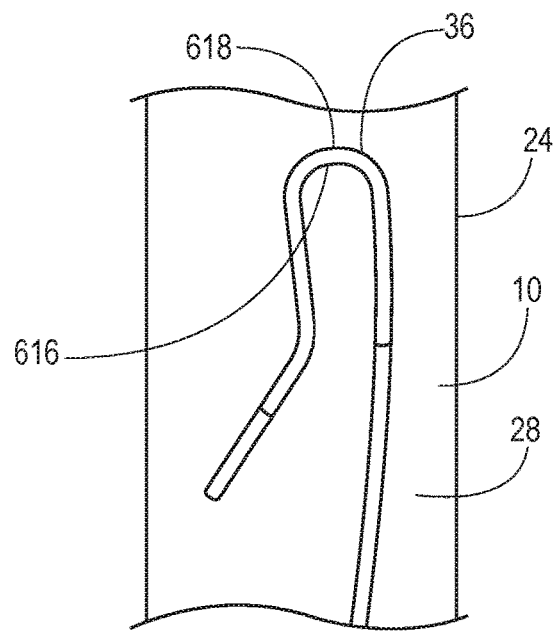
FIG. 35 shows the catheter after heat-setting.

In accord with one aspect of the catheter construction, the polymeric jacket 28 is heat set onto the hypotube 26 such that at least the axis of the curvature portion of the hypotube extends along a curve, with the inner, smaller radius, concave (lower) surface 616 of the hypotube curved under compression and the outer, larger radius, convex (upper)

surface 618 (along the apex side) of the hypotube curved under tension (FIG. 35). The resin is differentially heat set such that the resin at the lower surface of the central curvature segment 36 along the hypotube is raised to a temperature at or above the melting point of the resin, while the resin at the upper surface of the central curvature segment 36 is raised to a temperature below the melting point of the resin. The resin on the lower surface is able to fluidize, relieving residual compressive stress and distributing the resin evenly over the lower surface. The resin at the upper surface does not melt, preventing exposure of the underlying hypotube, as a resin under tension tends to thin over the upper surface. However, the resin at the upper surface is permitted to reach a plastic transformation temperature that relieves tensile stress in the material.

Figure 27:
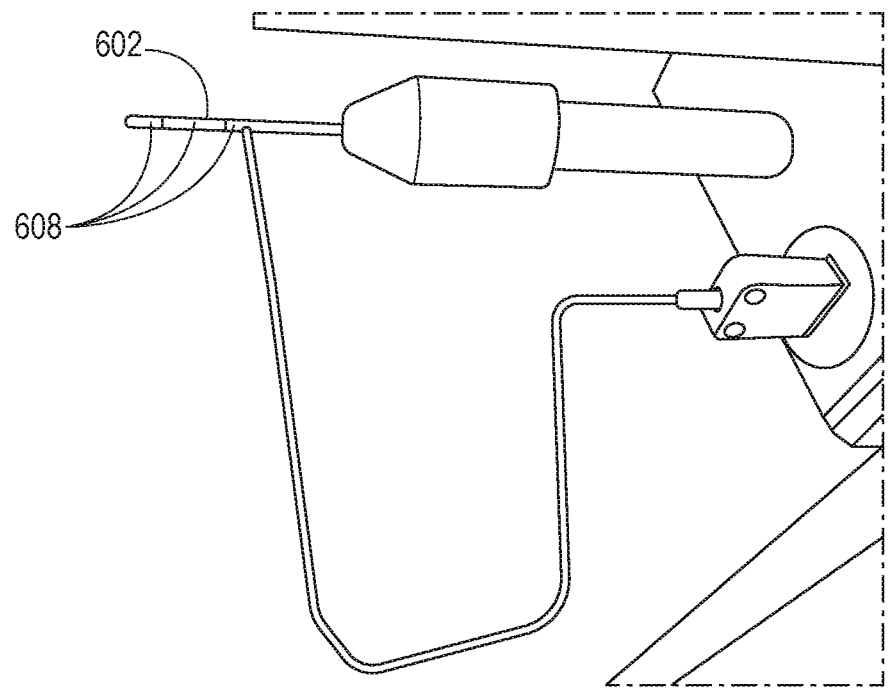
FIGS. 27 and 28 show a system for heat setting a polymer jacket over the shape-retentive distal end of the catheter.
Figure 28:
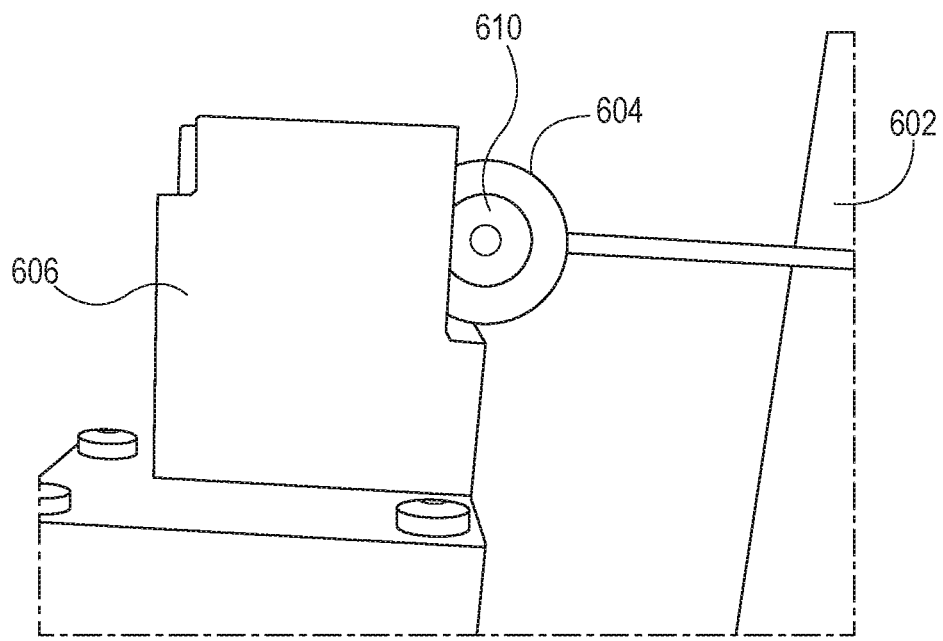
Figure 32:
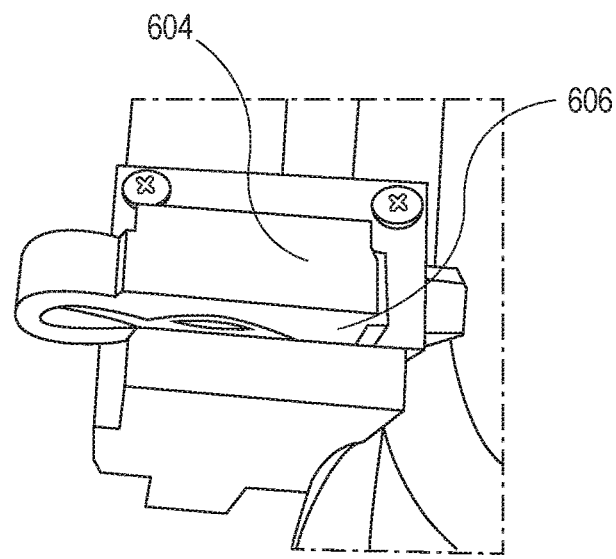
Figure 33:
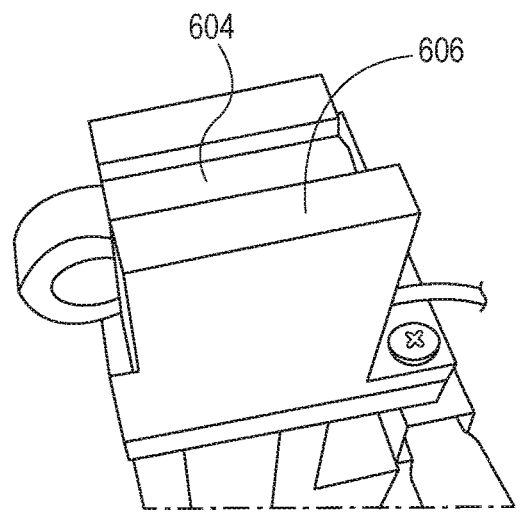

In one method of differential heat setting the resin of the jacket, heated air is utilized. The heating air is applied locally to the lower surface. Referring to FIGS. 27 and 28, a system is provided for directing the heated air to the lower surface for the heat setting procedure. The system includes a nozzle 602, a holder, preferably in the form of a shaping plate 604, and preferably a mount 606 that stably receives and orients the plate. The nozzle 602 includes perforations 608 ranging in size between 0.0005 inch and 0.015 inch in diameter. The holder 604 includes an opening 610 and a channel 612 sized to accommodate the distal shape-retentive section 24 at the distal end of the guiding catheter 10 (FIG. 29). Referring to FIGS. 30 and 31, the channel 612 defines a path in the shape at which the shape-retentive section is to be heated, with such path extending about the opening 610. Section 24 of the catheter is placed into the channel, with the central curvature segment 36 of the hypotube 26 aligning with the corresponding portion of the path and extending about the opening 610. The holder 604, with distal shape-retentive section 24 positioned therein, is then inserted into the mount 606. Referring back to FIG. 28, the nozzle 602 and holder 604 are then positioned relative to each other such that the nozzle 602 is positioned within the opening 610 of the holder, preferably without contacting the holder 604 or the catheter 10.

Figure 34:
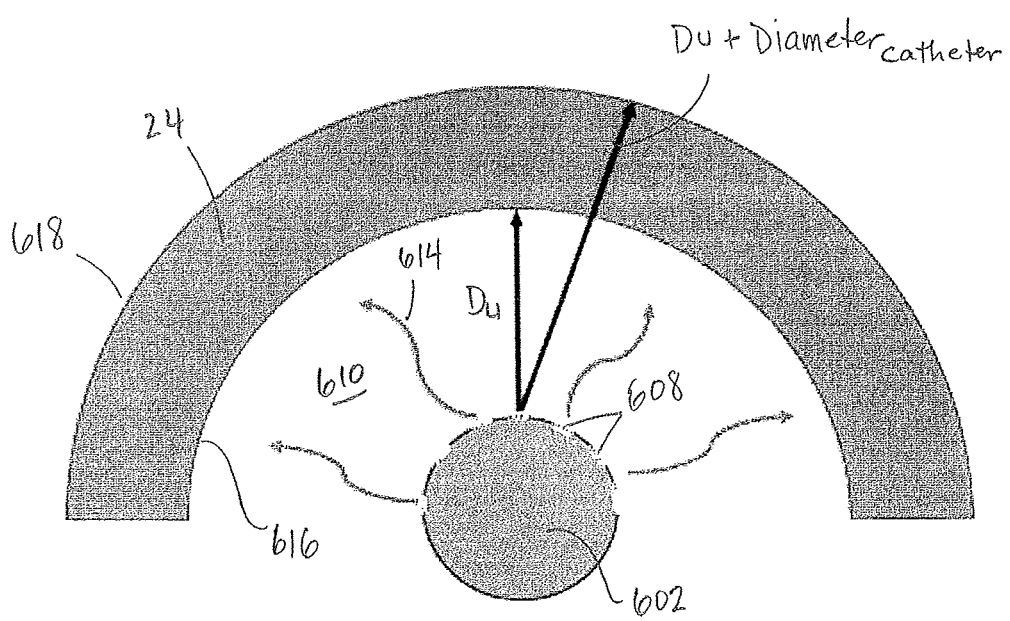

Referring to FIG. 34, air 614 is then passed through the nozzle 602 and out of the perforations 608. As air passes through the perforations 608, an even zone of heated air is produced. The air temperature forms a gradient with higher temperatures nearer the perforated nozzle 602 and lower temperatures extending away from the nozzle. This gradient is defined by mathematical modeling such as Newton's Law of Cooling. Therefore, the system is designed and operated in a manner where the temperature on the lower surface 616 of the curving segment 24 (and closest to the nozzle) reaches the melting point of the resin at a fixed distance from the perforated surface ($D_u$) while the temperature drops below the melting point of the resin on the upper surface 618 of the curving segment over the distance of the diameter of the catheter ($D_u$+Diameter$_{Catheter}$). After air heating, the catheter 10 is allowed to cool, and then removed from the holder 604, as shown in FIG. 35, with the intended shape retained.

In another method of differentially heat setting the resin outer jacket 28, radiant energy is used. The radiant energy is applied to melt the lower surface 616 while allowing the resin at the upper surface 618 to plastically deform. In an embodiment, an electrically heated element of fixed geometry is used within the opening of the holder of the system to perform the radiant heat setting operation. The radiant energy intensity near the element is higher than that farther from the element. The gradient of the radiant energy is predicted using mathematical models such as Newton's Inverse Square Law. Therefore, the system is designed and operated in a manner where the temperature on the lower surface 616 reaches the melting point of the resin at a fixed distance from the radiant surface ($D_u$) while the temperature drops below the melting point of the resin on the upper surface 618 over the distance of the diameter of the catheter ($D_u$+Diameter$_{Catheter}$).

As such, the gradient of heat over a specified distance and the transfer of heat into the resin relative to temperature and time can be modeled mathematically in both heating methods, and the heating apparatus takes such parameters into account by including a timing function that limits the duration of exposure to the heat.

Figure 36:
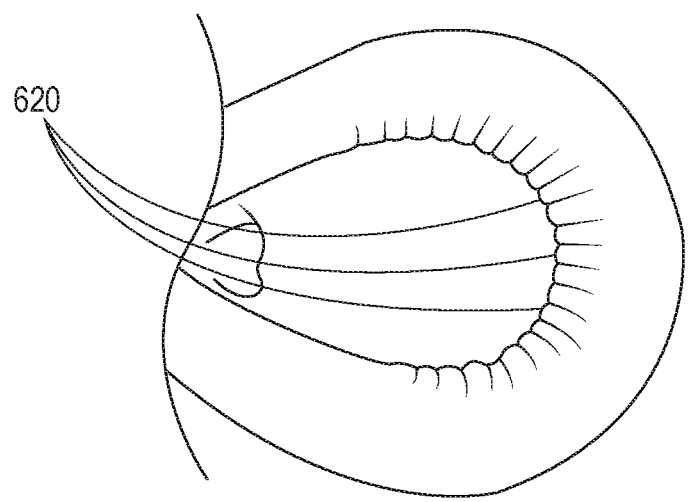
FIG. 36 is an enlarged view showing features of the catheter prior to heat-setting.
Figure 37:
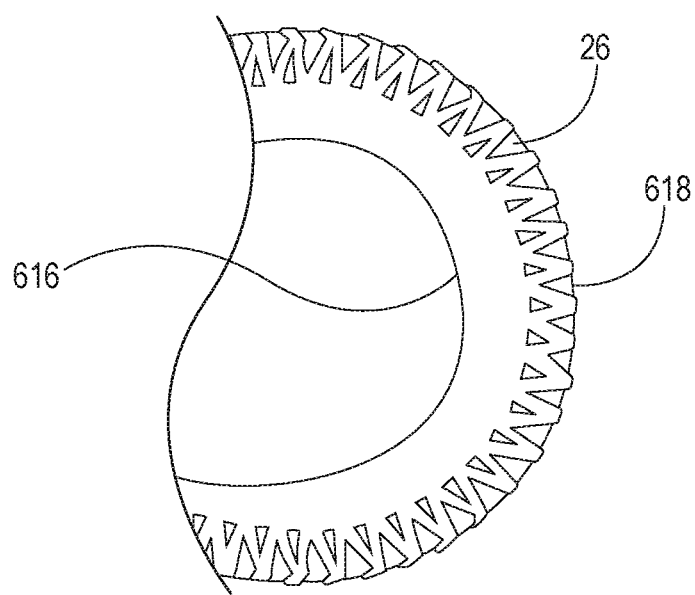
FIG. 37 is an enlarged view showing features of the catheter after heat-setting.

In both of these cases, the resin on the lower surface 616 fluidizes, fully relieving the residual compressive stress existing in the resin beforehand, shown by the folds 620 at the lower surface 616 of the pre-treated catheter 10 in FIG. 36, and distributing the resin evenly over the lower surface 616 in the post-treated catheter shown in FIG. 37. The resin on the upper surface 618 does not melt and fluidize. This prevents exposure of the underlying hypotube 26 as the resin under tension tends to thin over the upper surface. Based on the gradient formed by the convective or radiant elements, the resin is allowed to reach the plastic transformation temperature where the tensile stress can be relieved by plastic deformation.

The resin jacket 508 is preferentially made of a polymer acting in a primarily elastic manner in the room temperature to body temperature range. The resin is also preferentially made of a thermoplastic material (one that can move or fluidize at elevated temperatures) as opposed to a thermoset (a material with polymer crosslinking or otherwise cannot be fluidized by elevated temperatures).

Where radiopacity is required, the resin may be loaded with radiopacifying agents such as barium sulfate ($BaSO_4$), bismuth oxide ($Bi_2O_3$), or metallic powders such as tungsten.

Figure 46:
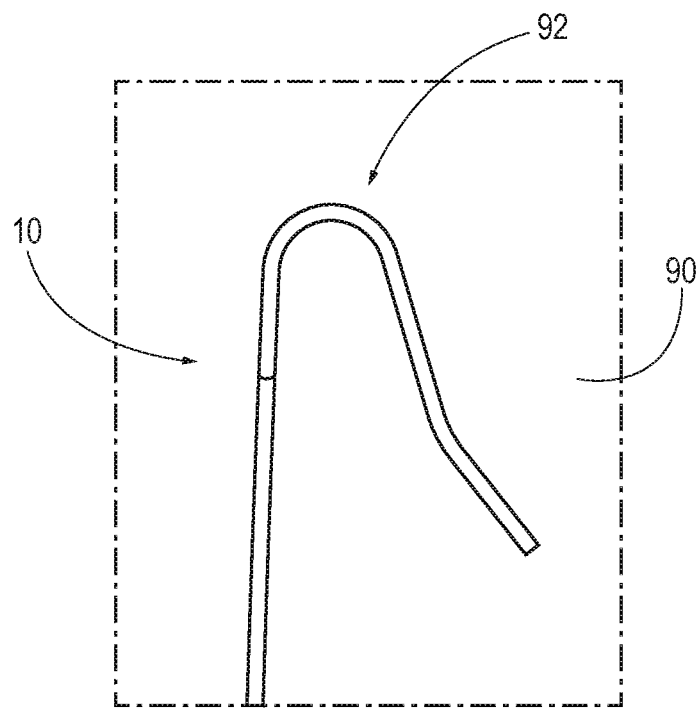
FIG. 46 illustrates an embodiment of the guiding catheter in a natural unbiased configuration.
Figure 47:
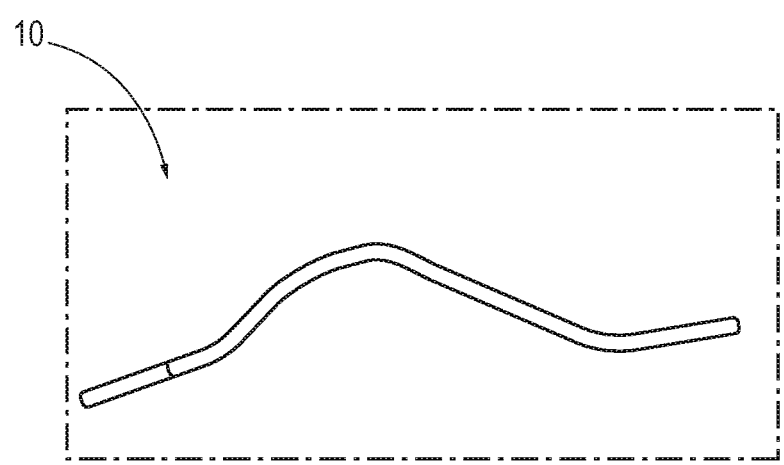
FIG. 47 illustrates the guiding catheter of FIG. 46 straightened for insertion into a vessel.

Turning now to FIG. 46, the guiding catheter 10 is shown in its at rest position with shaped with two curved regions at its distal end, a distal curve 90 and a primary curve 92. FIG. 47 shows the guiding catheter 10 straightened for insertion into a delivery catheter and through vessels, such that the distal end adopts an S-shape.

Figure 48:
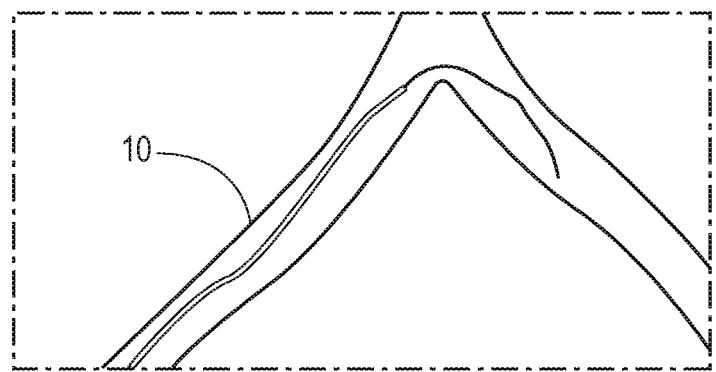
FIGS. 48 through 50 illustrate one method of inserting the guiding catheter of FIGS. 46 and 47.
Figure 49:
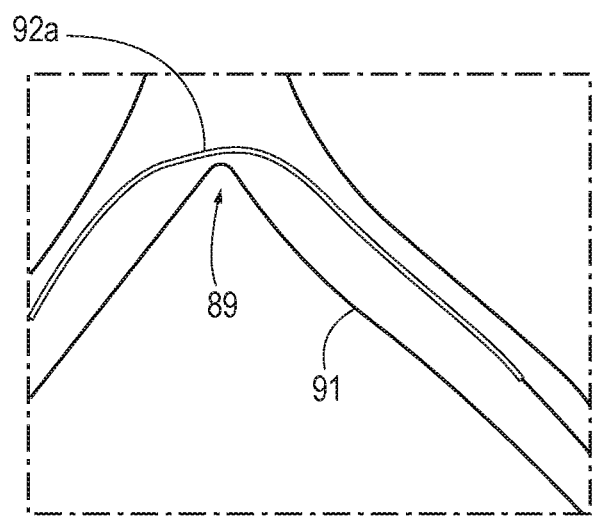
Figure 50:
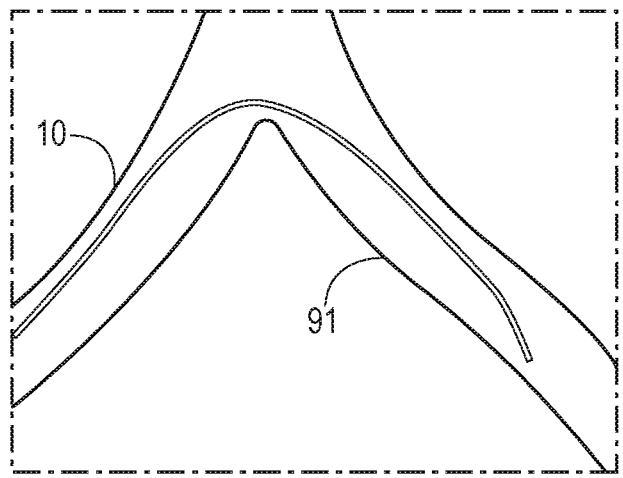

Referring to FIGS. 48 through 50, in a method, the guiding catheter 10 is tracked over a guidewire 88 into an anatomical arch 89 (such as the iliac arch). It is often easier to position the guidewire 88 over the arch 89 into the descending vessel 91 when the distal curve 90 of the guiding catheter conforms to the curve of the arch. However, if inserted in this manner, the guiding catheter 10 will follow the path of the distal curve 90, causing the hyperextension at 92a (bending backwards) of the primary curve 92. The guiding catheter cannot properly configure in this orientation. Therefore, to correctly reorient the device, the device must be rotated by 180 degrees. Once the rotation is effected, the required shape is formed and the catheter 10 can be advanced according to standard procedure.

Figure 51:
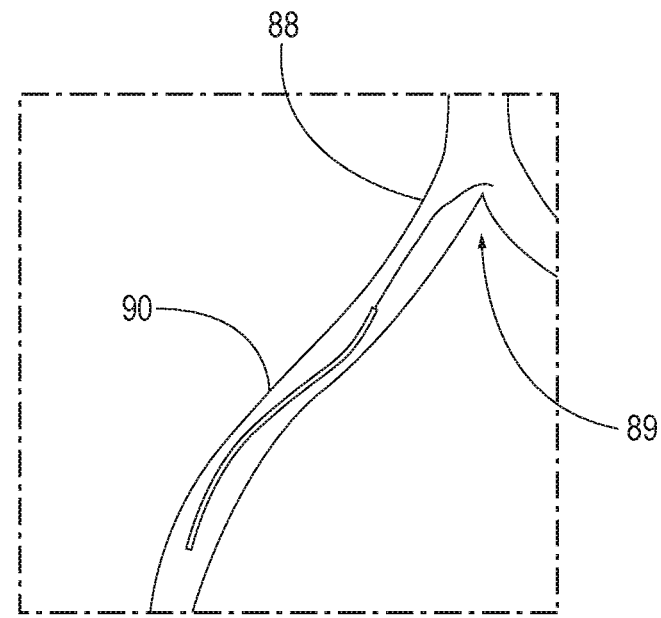
FIGS. 51 and 52 illustrate another method of inserting the guiding catheter of FIGS. 46 and 47.
Figure 52:
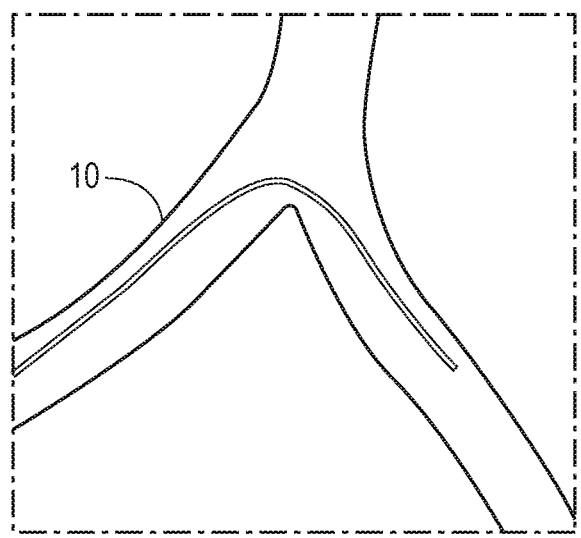

Turning to FIGS. 51 and 52, in another method, the guiding catheter 10 can be tracked over a guidewire 88 through the anatomical arch 89 and initially in the correct orientation by tracking with the distal curve 90 pointed upward during advancement. In this manner, hyperextension of the primary curve 92 through the arch 89 is prevented and there is no need to rotate the guiding catheter 10 to correctly orient it within the descending vessel 91 (FIG. 52).

Both of the prior methods can be carried out with a catheter having a hypotube with a biased-spine construct using the aforementioned biasing techniques (either with stronger struts or heat-set struts, e.g., as shown in FIGS. 40A and 40B).

However, using a catheter having a hypotube with a non-biased spine construct (such as shown in FIG. 39A) or with a construct having a gradient of forces (such as shown in FIG. 39B), the device can be tracked over the arch in any direction; however, the gradient of forces will result in a rotation of the device to minimize force and position the primary curvature in confirmation with the arch. Similarly, the design shown in FIGS. 41A and 41B will also autocorrect in shape. 52

There have been described and illustrated herein embodiments of a catheter and methods of manufacturing the catheter. In addition, while embodiments of a pattern-cut elastic tube, which is more preferably superelastic and in the form of a hypotube, is described for use in catheter, it is recognized that the elastic tube has utility beyond use in a catheter and can be used in other medical devices, including, by way of example only, guidewires, vascular treatment devices, endoscopic instruments, neurological treatment devices, and many other devices. While particular embodiments of the invention have been described, it is not intended that the invention be limited thereto, as it is intended that the invention be as broad in scope as the art will allow and that the specification be read likewise. It will therefore be appreciated by those skilled in the art that yet other modifications could be made to the provided invention without deviating from its scope as claimed.

What is claimed is:

1. A catheter, comprising:
   a) a tubular braided first portion having proximal and distal ends;
   b) a tubular second portion having proximal and distal ends, the proximal end of the second portion coupled to the distal end of the first portion and having increased flexiblity in at least one direction relative to the first portion; and
   c) a joint at a butt of the distal end of the first portion and the proximal end of the second portion, the joint having proximal, central, and distal joint segments,
   the proximal and distal joint segments having a flexural modulus one-half to two-thirds that of a flexural modulus of the central segment.

2. The catheter of claim 1, further comprising:
a jacket over the joint, the jacket including a lower durometer resin at the proximal and distal joint segment, and a higher durometer resin at the central joint segment.

3. The catheter of claim 1, further comprising:
a high durometer extrusion over the central joint segment; and
a resin jacket over the proximal, central and distal joint segments and the extrusion.

4. The catheter of claim 1, wherein:
the proximal and distal joint segments having a kink radius one-half to two-thirds of a kink radius of the central joint segment.

5. The catheter of claim 4, wherein:
the kink radius is a minimum of 3 mm.

6. The catheter of claim 1, wherein:
during bending centered at the joint, the proximal and distal segments undergo higher deformation than the central segment undergoes.

7. The catheter of claim 1, wherein:
during bending centered at the joint, the central segment remains relatively more rigid than the proximal and distal segments.

8. The catheter of claim 1, wherein:
the proximal and distal joint segments are jacketed in a low durometer resin, and the central joint segment is jacketed in a relatively higher durometer resin that the lower durometer resin.

9. The catheter of claim 8, wherein:
the low durometer resin has a durometer of 60A to 55D durometer.

10. The catheter of claim 9, wherein:
the higher durometer resin has a 10 to 60 durometer higher than the low durometer resin.

11. The catheter of claim 1, wherein:
the central segment is reinforced with an adhesive, and the proximal, central and distal segments are then covered in an elastomeric resin.

12. The catheter of claim 1, wherein:
the central segment is provided with a tubular extrusion or wrap, and the proximal, central and distal segments are then covered in an elastomeric resin tube or wrap.

13. The catheter of claim 12, wherein:
the tubular extrusion or wrap is made of polytetrafluoroethylene (PTFE), fluorinated ethylene propylene (FEP), perfluoroalkoxy (PFA), ethylene tetrafluoroethylene (ETFE), polyethylene terephthalate (PET), and/or polyetherether-ketone (PEEK) polymers.

* * * * *